US011457169B2

(12) United States Patent
Kawasaki

(10) Patent No.: US 11,457,169 B2
(45) Date of Patent: Sep. 27, 2022

(54) SOLID-STATE IMAGING ELEMENT AND ELECTRONIC EQUIPMENT

(71) Applicant: SONY SEMICONDUCTOR SOLUTIONS CORPORATION, Kanagawa (JP)

(72) Inventor: Ryohei Kawasaki, Kanagawa (JP)

(73) Assignee: SONY SEMICONDUCTOR SOLUTIONS CORPORATION, Kanagawa (JP)

( * ) Notice: Subject to any disclaimer, the term of this patent is extended or adjusted under 35 U.S.C. 154(b) by 0 days.

(21) Appl. No.: 17/305,189

(22) Filed: Jul. 1, 2021

(65) Prior Publication Data

US 2021/0329186 A1  Oct. 21, 2021

Related U.S. Application Data

(63) Continuation of application No. 16/475,290, filed as application No. PCT/JP2017/047265 on Dec. 28, 2017, now Pat. No. 11,082,654.

(30) Foreign Application Priority Data

Jan. 13, 2017 (JP) ................................ 2017-004081

(51) Int. Cl.
*H04N 5/378* (2011.01)
*H04N 5/3745* (2011.01)
(Continued)

(52) U.S. Cl.
CPC ............ *H04N 5/378* (2013.01); *H04N 5/374* (2013.01); *H04N 5/379* (2018.08); *H04N 5/37455* (2013.01)

(58) Field of Classification Search
CPC ............ H04N 5/3745; H04N 5/37455; H04N 5/37457; H04N 5/378; H04N 5/379
See application file for complete search history.

(56) References Cited

U.S. PATENT DOCUMENTS

| 11,082,654 B2 * | 8/2021 | Kawasaki ............... A61B 1/05 |
| 2017/0237928 A1 | 8/2017 | Kusano |

(Continued)

FOREIGN PATENT DOCUMENTS

| CN | 101409772 A | 4/2009 |
| CN | 101719994 A | 6/2010 |

(Continued)

OTHER PUBLICATIONS

Office Action for CN Patent Application No. 201780082438.0, dated Apr. 2, 2021, 06 pages of English Translation and 06 pages of Office Action.

(Continued)

*Primary Examiner* — Daniel M Pasiewicz
(74) *Attorney, Agent, or Firm* — Chip Law Group

(57) ABSTRACT

The present disclosure relates to a solid-state imaging element and electronic equipment that make it possible to sufficiently secure a time width of a pulse signal. In an AD converter for each unit pixel, a pulse generation circuit feeds back a delay signal obtained by delaying an output signal of the comparator to the comparator and arithmetically operates the output signal and the delay signal to generate a pulse signal. A latch circuit latches the pulse signal generated by the pulse generation circuit. The present disclosure can be applied to a solid-state imaging element of a stacked type and a back side illumination type.

9 Claims, 22 Drawing Sheets

(51) Int. Cl.
*H04N 5/374* (2011.01)
*H04N 5/369* (2011.01)

(56) References Cited

U.S. PATENT DOCUMENTS

| | | |
|---|---|---|
| 2017/0272678 A1 | 9/2017 | Sakakibara et al. |
| 2017/0318250 A1 | 11/2017 | Sakakibara et al. |

FOREIGN PATENT DOCUMENTS

| | | |
|---|---|---|
| CN | 101783863 A | 7/2010 |
| CN | 107005665 A | 8/2017 |
| JP | 2016-092661 A | 5/2016 |
| WO | 2002/095679 A2 | 11/2002 |
| WO | 2016/009832 A1 | 1/2016 |
| WO | 2016/104174 A1 | 6/2016 |
| WO | 2016/136448 A1 | 9/2016 |

OTHER PUBLICATIONS

International Search Report and Written Opinion of PCT Application No. PCT/JP2017/047265, dated Mar. 20, 2018, 07 pages of English Translation and 07 pages of ISRWO.
International Preliminary Report on Patentability of PCT Application No. PCT/JP2017/047265, dated Jul. 25, 2019, 08 pages of English Translation and 04 pages of IPRP.
Notice of Allowance for U.S. Appl. No. 16/475,290, dated Jul. 7, 2021, 2 pages.
Notice of Allowance for U.S. Appl. No. 16/475,290, dated Mar. 30, 2021, 10 pages.

\* cited by examiner

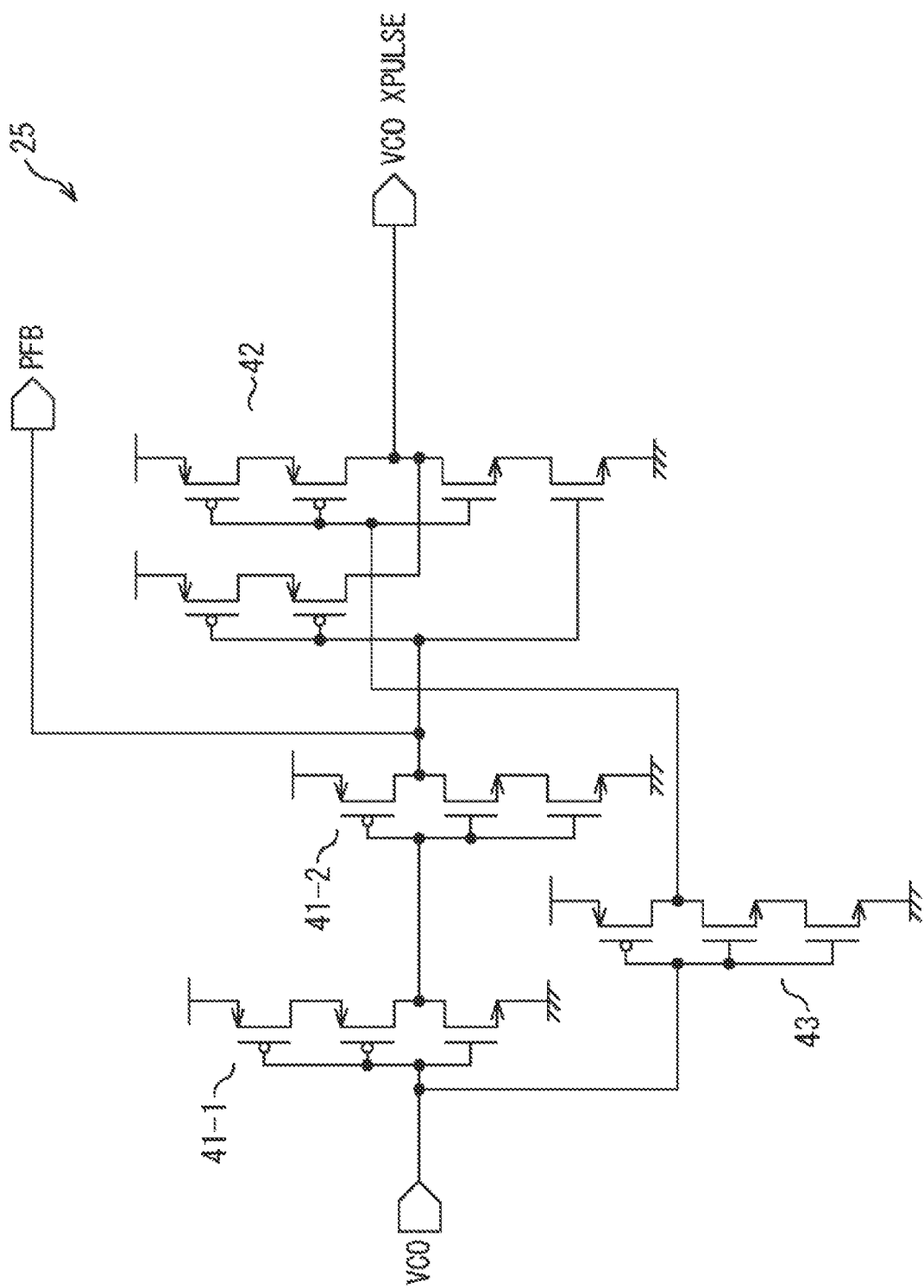
F I G . 1 2

SOLID-STATE IMAGING ELEMENT AND ELECTRONIC EQUIPMENT

CROSS REFERENCE TO RELATED APPLICATIONS

This application is continuation application of U.S. patent application Ser. No. 16/475,290, filed on Jul. 1, 2019, which is a U.S. National Phase of International Patent Application No. PCT/JP2017/047265 filed on Dec. 28, 2017, which claims priority benefit of Japanese Patent Application No. JP 2017-004081 filed in the Japan Patent Office on Jan. 13, 2017. Each of the above-referenced applications is hereby incorporated herein by reference in its entirety.

TECHNICAL FIELD

The present disclosure relates to a solid-state imaging element and electronic equipment, and particularly relates to a solid-state imaging element and electronic equipment that make it possible to sufficiently secure a time width of a pulse signal.

BACKGROUND ART

A system has been proposed in which, in order to allow an imaging element, in which pixels are disposed two-dimensionally, to deal with speeding up of image signal outputting, an analog to digital conversion device is disposed in each pixel such that analog to digital conversion is performed simultaneously by all pixels to speed up analog to digital conversion. In this system, a comparison section compares an analog image signal and a reference signal with each other. Then, when the voltage of the reference signal transits from a state in which it is lower than the voltage of the analog image signal to a state in which it is higher than the voltage of the analog image signal or from a state in which it is higher the voltage of the analog image signal to a state in which it is lower the voltage of the analog image signal, this voltage change is detected and outputted as a comparison result. Further, a digital code corresponding to the voltage of the reference signal is inputted to a latch circuit, and the inputted digital code is retained by the latch circuit on the basis of the detection result by the comparison circuit. Thereafter, the digital code retained in the latch circuit is outputted as the result of the analog to digital conversion.

The imaging device in PTL 1 is configured such that it has a function for feeding back an output signal of the comparator into the comparator in order to accelerate the signal transition in the comparator. Then, an effective Window is provided using the signal, and the start and the end of a data validity period of the latch circuit is adjusted.

CITATION LIST

Patent Literature

[PTL 1]
WO 2016/136448

SUMMARY

Technical Problem

However, in order to secure such a pulse width sufficient to allow a signal from a repeater to be acquired, it is necessary to increase a circuit area.

The present disclosure has been made in view of such a situation as described above and makes it possible to sufficiently secure a time width of a pulse signal.

Solution to Problem

A solid-state imaging element according to one aspect of the present technology includes a pixel array section in which unit pixels each having a photoelectric conversion section are disposed, and an AD converter for each of the unit pixels, in which the AD converter includes a pulse generation circuit that feeds back a delay signal obtained by delaying an output signal of a comparator to the comparator and performs arithmetic operation of the output signal and the delay signal to generate a pulse signal, and a latch circuit that latches a data code using the pulse signal generated by the pulse generation circuit.

The pulse generation circuit may include a delay element that delays the output signal of the comparator to generate the delay signal, and an arithmetic element that arithmetically operates the output signal and the delay signal to generate the pulse signal.

The arithmetic element includes a NOR circuit.

The arithmetic element includes a NAND circuit.

In the pulse generation circuit, a logical threshold value of a gate element is adjusted.

In the pulse generation circuit, the logical threshold value of the gate element is adjusted by changing an element number of transistors.

In the pulse generation circuit, the logical threshold value of the gate element is adjusted by setting the threshold value of each of the elements of transistors to a high threshold value and a low threshold value.

The pulse generation circuit may further include a selection circuit that selects a path used when a delay signal obtained by delaying the output signal of the comparator is to be fed back to the comparator and the output signal and the delay signal are arithmetically operated to generate a pulse signal and another path used when the output signal of the comparator is to be used as it is.

Electronic equipment according to the one aspect of the present technology includes: a solid-state imaging element including a pixel array section in which unit pixels each having a photoelectric conversion section are disposed, and an AD converter for each of the unit pixels, in which the AD converter includes a pulse generation circuit that feeds back a delay signal obtained by delaying an output signal of a comparator to the comparator and performs arithmetic operation of the output signal and the delay signal to generate a pulse signal, and a latch circuit that latches a data code using the pulse signal generated by the pulse generation circuit; a signal processing circuit that processes an output signal outputted from the solid-state imaging element; and an optical system that enters incident light into the solid-state imaging element.

In the one aspect of the present technology, a delay signal formed by delaying an output signal of the comparator by the AD converter of each of the unit pixels, which are disposed in the pixel array section and each include the photoelectric conversion section, is fed back to the comparator, and the output signal and the delay signal are arithmetically operated to generate a pulse signal. Then, a data code is latched using the generated pulse signal.

Advantageous Effects of Invention

With the present technology, a time width of a pulse signal can be secured sufficiently.

It is to be noted that the advantageous effects described in the present specification are merely examples, and the advantageous effects of the present technology are not restricted to the advantageous effects described in the present specification and there may be additional advantageous effects.

BRIEF DESCRIPTION OF DRAWINGS

FIG. 12 is a circuit diagram depicting a configuration example of the pulse generation circuit of FIG. 9 in the case where a NAND circuit is used as an arithmetic element.

DESCRIPTION OF EMBODIMENT

In the following, a mode for carrying out the present disclosure (hereinafter referred to as an embodiment) is described. It is to be noted that the description is given in the following order.

0. Description of Device
1. Embodiment
2. Example of Use of Image Sensor
3. Example of Electronic Equipment
4. Application Example to In-Vivo Information Acquisition System
5. Application Example to Endoscopic Surgery System
6. Application Example to Moving Body 0. Description of Device <Schematic Configuration Example of Solid-State Imaging Device>

Figure 1:
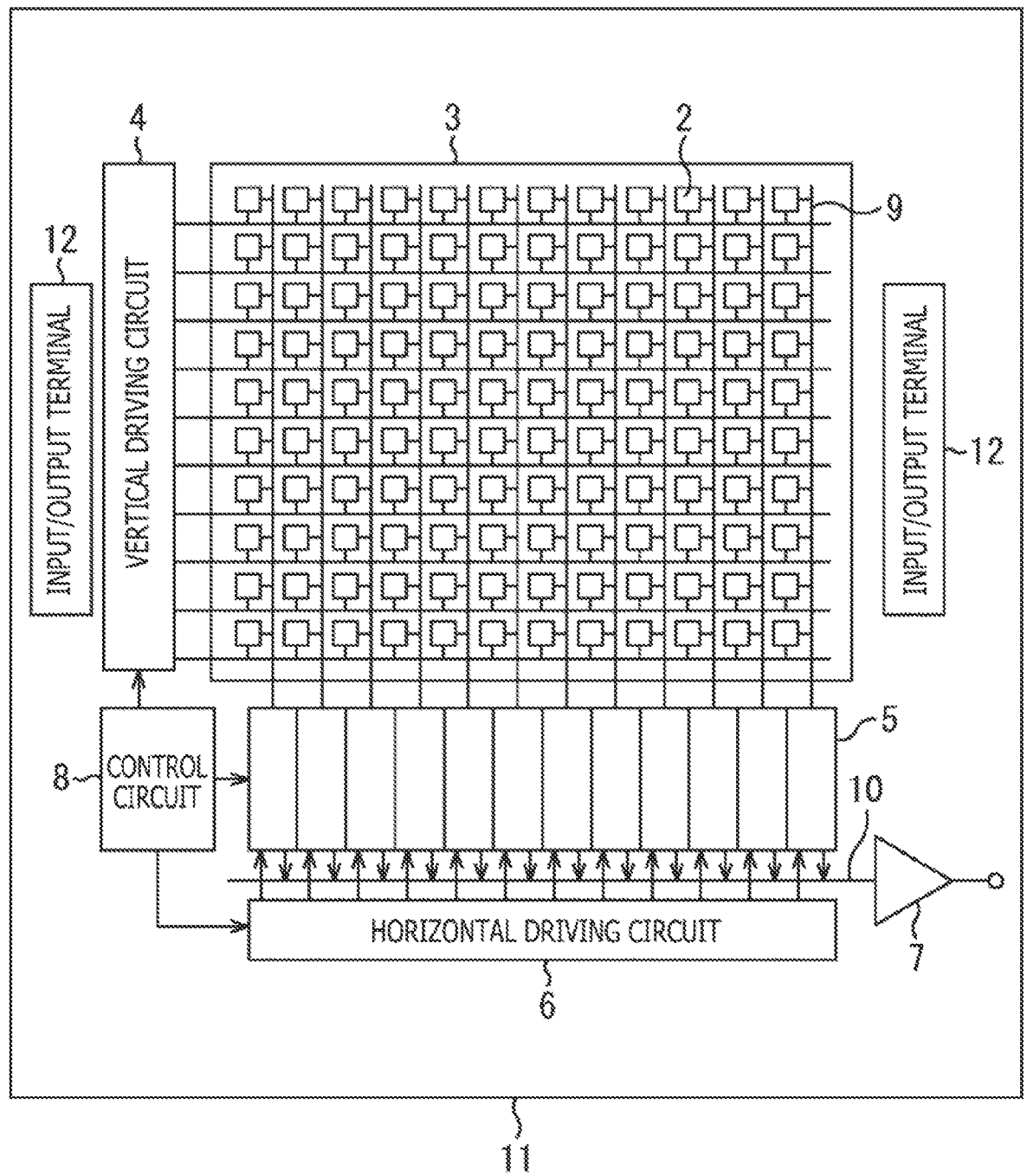
FIG. 1 is a block diagram depicting a general configuration example of a solid-state imaging element to which the present technology is applied.

FIG. 1 depicts a schematic configuration example of one example of a CMOS (Complementary Metal Oxide Semiconductor) solid-state imaging element applied to embodiments of the present technology.

As depicted in FIG. 1, a solid-state imaging element (element chip) 1 includes a pixel region (so-called imaging region) 3 in which a plurality of pixels 2 each including a photoelectric conversion element is arrayed regularly and two-dimensionally on a semiconductor substrate 11 (for example, a silicon substrate), and a peripheral circuit region.

Each pixel 2 includes a photoelectric conversion element (for example, a PD (Photo Diode)) and a plurality of pixel transistors (so-called MOS transistors). The plurality of pixel transistors can include, for example, three transistors of a transfer transistor, a reset transistor, and an amplification transistor. Also, the plurality of pixel transistors can include four transistors, further adding a selection transistor to the three transistors above.

Also it is possible for the pixels 2 to have a shared pixel structure. The shared pixel structure includes a plurality of photodiodes, a plurality of transfer transistors, a single shared floating diffusion, and other pixel transistors shared one by one. The photodiodes are photoelectric conversion elements.

The peripheral circuit region includes a vertical driving circuit 4, a column signal processing circuit 5, a horizontal driving circuit 6, an outputting circuit 7, and a control circuit 8.

The control circuit 8 receives an input clock and data that instructs an operation mode and so forth and outputs data of internal information and so forth of the solid-state imaging element 1. In particular, the control circuit 8 generates a clock signal that becomes a reference to operation of the vertical driving circuit 4, the column signal processing circuit 5, and the horizontal driving circuit 6, and a control signal on the basis of a vertical synchronizing signal, a horizontal synchronizing signal and a master clock. Then, the control circuit 8 inputs the signals to the vertical driving circuit 4, the column signal processing circuit 5, and the horizontal driving circuit 6.

The vertical driving circuit 4 is configured, for example, from a shift register, and selects a pixel driving wiring line and supplies a pulse for driving a pixel 2 to the selected pixel driving line to drive pixels 2 in units of rows. In particular, the vertical driving circuit 4 selectively scans the pixels 2 of the pixel array 3 in units of rows successively in a vertical direction and supplies a pixel signal based on a signal charge generated in response to a received light amount, for example, at the photoelectric conversion element of each of the pixels 2 through a vertical signal line 9 to the column signal processing circuit 5.

The column signal processing circuit 5 is disposed, for example, for each column of the pixels 2 and performs signal processing of signals outputted from the pixels 2 for one row such as noise removal for each pixel column. In particular, the column signal processing circuit 5 performs signal processing such as CDS (Correlated Double Sampling) for removing fixed pattern noise unique to the pixels 2, signal amplification, A/D (Analog/Digital) conversion, and so forth. A horizontal selection switch (not depicted) is provided in the output stage of the column signal processing circuit 5 such that it is connected between the column signal processing circuit 5 and a horizontal signal line 10. It is to be noted that part of the signal processing described above may be processed for each pixel.

The horizontal driving circuit 6 is configured, for example, from a shift register, and sequentially outputs a horizontal scanning pulse to select each of the column signal processing circuits 5, and then, a pixel signal is outputted from each of the column signal processing circuits 5 to the horizontal signal line 10.

The outputting circuit 7 performs signal processing for each of signals successively supplied from the column signal processing circuits 5 through the horizontal signal line 10 and outputs a resulting signal. For example, the outputting circuit 7 sometimes performs only buffering or sometimes performs black level adjustment, column dispersion correction, various digital signal processes and so forth.

Input/output terminals 12 are provided to transfer a signal to and from the outside.

1. Embodiment

<Structure Example of Solid-State Imaging Element>

Figure 2:
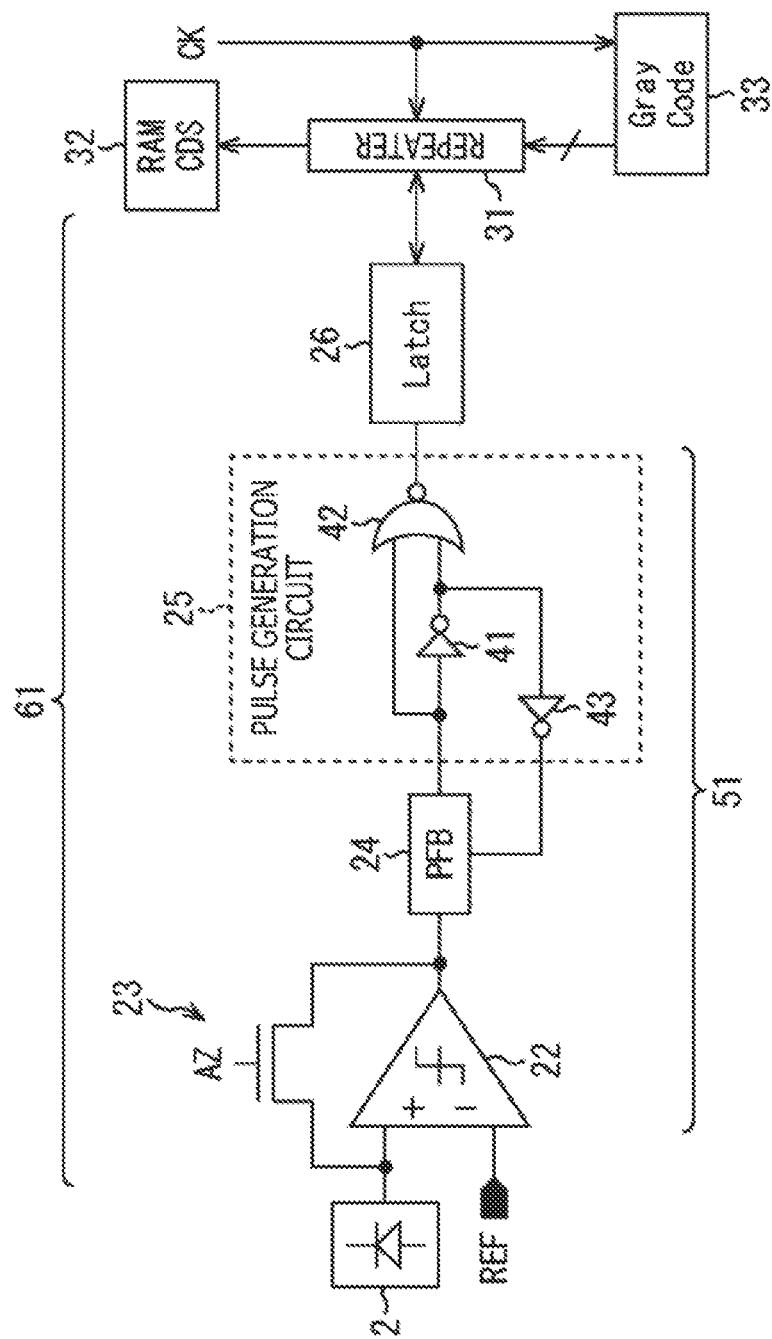
FIG. 2 is a block diagram depicting a configuration example of part of the solid-state imaging element to which the present technology is applied.

FIG. 2 is a block diagram depicting a configuration example of part of a solid-state imaging element to which the present technology is applied. The present technology is applied to a solid-state imaging element not of the example that includes an AD conversion device for each column as depicted in FIG. 1 but of an example in which an AD (Analog-Digital) conversion device 61 is provided for each pixel 2.

In the example of FIG. 2, a pixel 2 and an AD conversion device 61 that receives a pixel signal from the pixel 2 and a reference signal from a control circuit 8 as inputs thereto and converts them into digital signals as well as a repeater 31, a RAM CDS 32 and a Gray Code 33 that are disposed for each predetermined pixel column in the subsequent stage to the AD conversion device 61 are depicted. It is to be noted that the AD conversion device 61 is configured particularly from an AD converter 51 and a latch circuit 26.

The AD conversion device 61 includes a comparison circuit 22, an auto zero (AZ) 23, a PFB (Positive Feed Back) 24, a pulse generation circuit 25, and a latch circuit 26. The comparison circuit 22 receives a pixel signal and a reference signal as inputs thereto and outputs a result of comparison of them to the PFB 24. The auto zero 23 has a function for resetting the comparison circuit 22. The PFB 24 is a speeding up circuit, and receives an inversion signal from the comparison circuit 22 and a feedback (Feed Back) signal from the pulse generation circuit 25 as inputs thereto and outputs a comparison signal to the pulse generation circuit 25 of the subsequent stage.

The pulse generation circuit 25 includes a delay element 41, an arithmetic element 42, and an inversion element 43. The pulse generation circuit 25 performs delay arithmetic operation for providing an effective Window for acquiring data and receives the inversion signal and a delay signal obtained by delaying the inversion signal as inputs thereto to generate a pulse signal (VCO PULSE). Then, the pulse generation circuit 25 outputs the generated pulse signal to the latch circuit 26, and inverts the delay signal and feeds back the inverted delay signal as a feedback signal to the PFB 24. The latch circuit 26 stores a data code using the pulse signal for a predetermined period of time and outputs the stored data code to the repeater 31.

Figure 3:
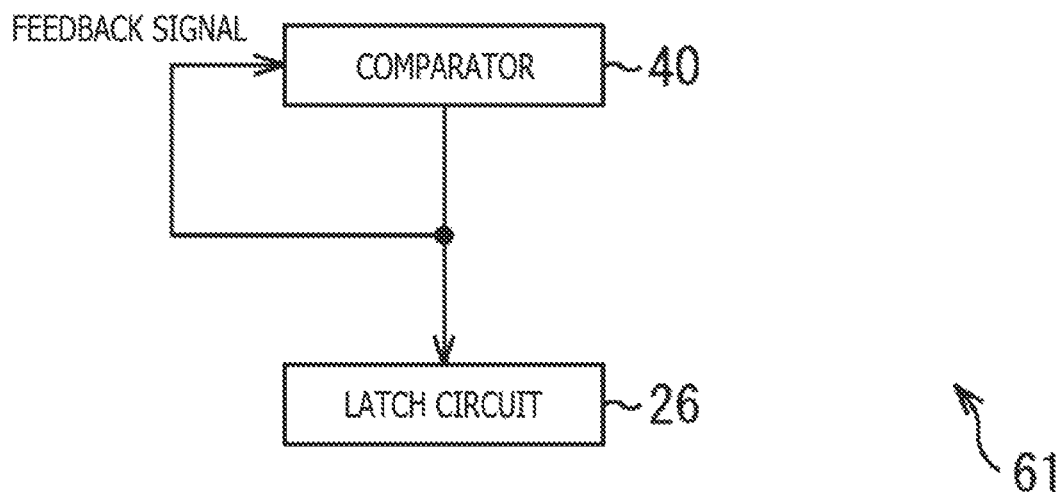
FIG. 3 is a view depicting a configuration example of an AD conversion device.
Figure 4:
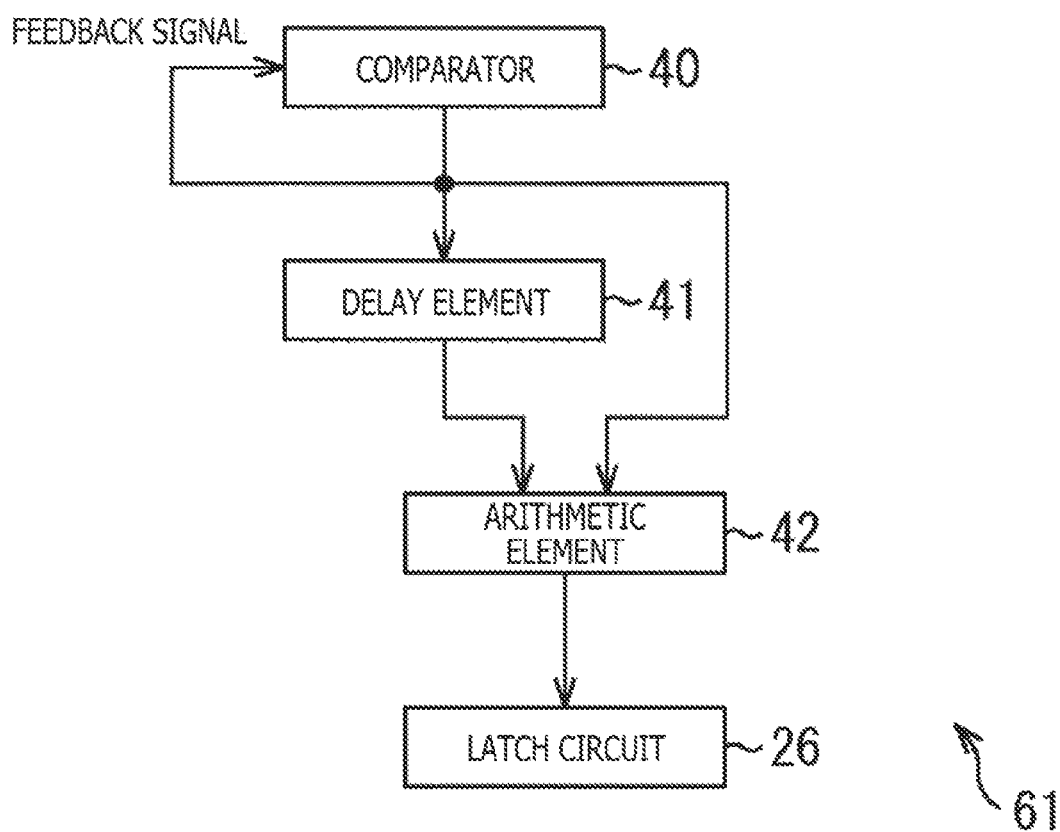
FIG. 4 is a view depicting another configuration example of the AD conversion device.
Figure 5:
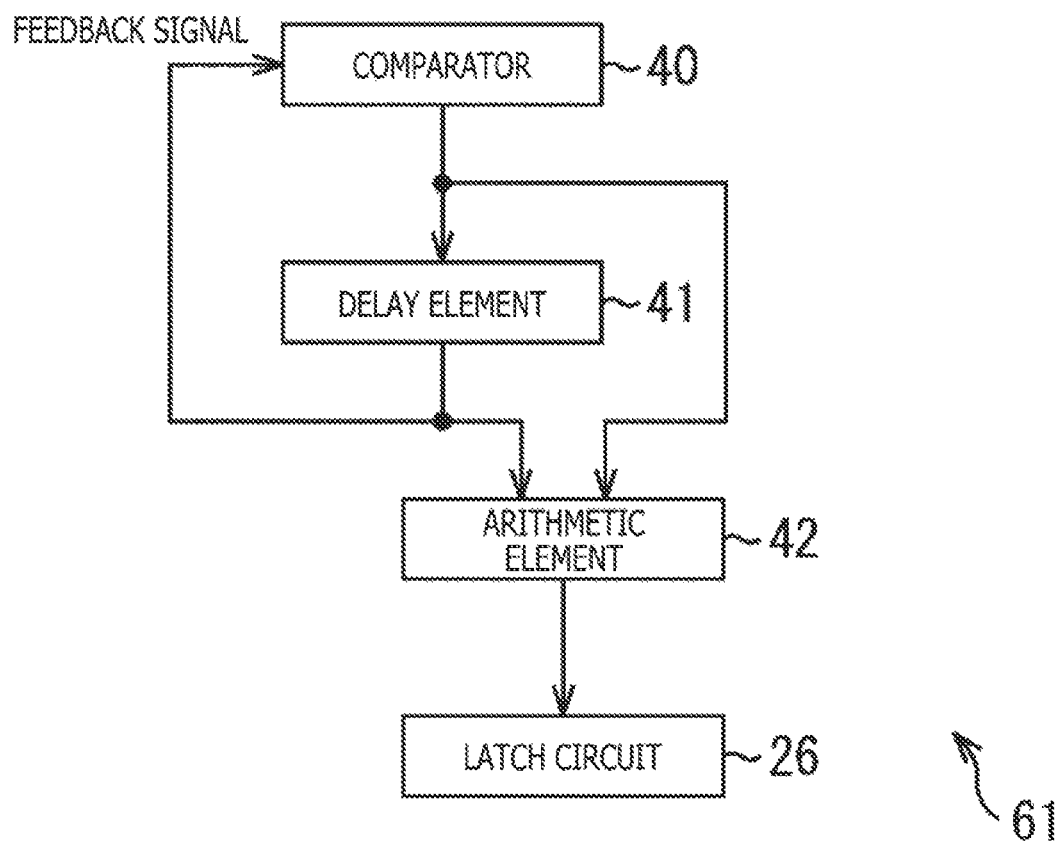
FIG. 5 is a view depicting a configuration example of an AD conversion device to which the present technology is applied.

In particular, in PTL 1, the AD conversion device 61 is configured such that a comparison signal from a comparator 40 is fed back as a feedback signal to the comparison circuit 22 as depicted in FIG. 3. It is to be noted that the comparator 40 includes the comparison circuit 22 and the PFB 24. Meanwhile, although the AD conversion device 61 of the example of FIG. 4 it includes the delay element 41 and the arithmetic element 42, even if the delay element 41 is provided, a comparison signal from the comparator 40 is fed back to the comparator 40 in front of the delay element 41.

On the other hand, in the AD conversion device 61 to which the present technology is applied, a delay signal after delay arithmetic operation is completed through the delay element 41 is used as a feedback signal that is fed back to the comparator 40.

Consequently, a feedback function for accelerating inversion transition of an output of the comparator 40 and a pulse generation function sufficient to acquire a signal from the repeater 31 using a delay signal are both achieved.

Figure 6:
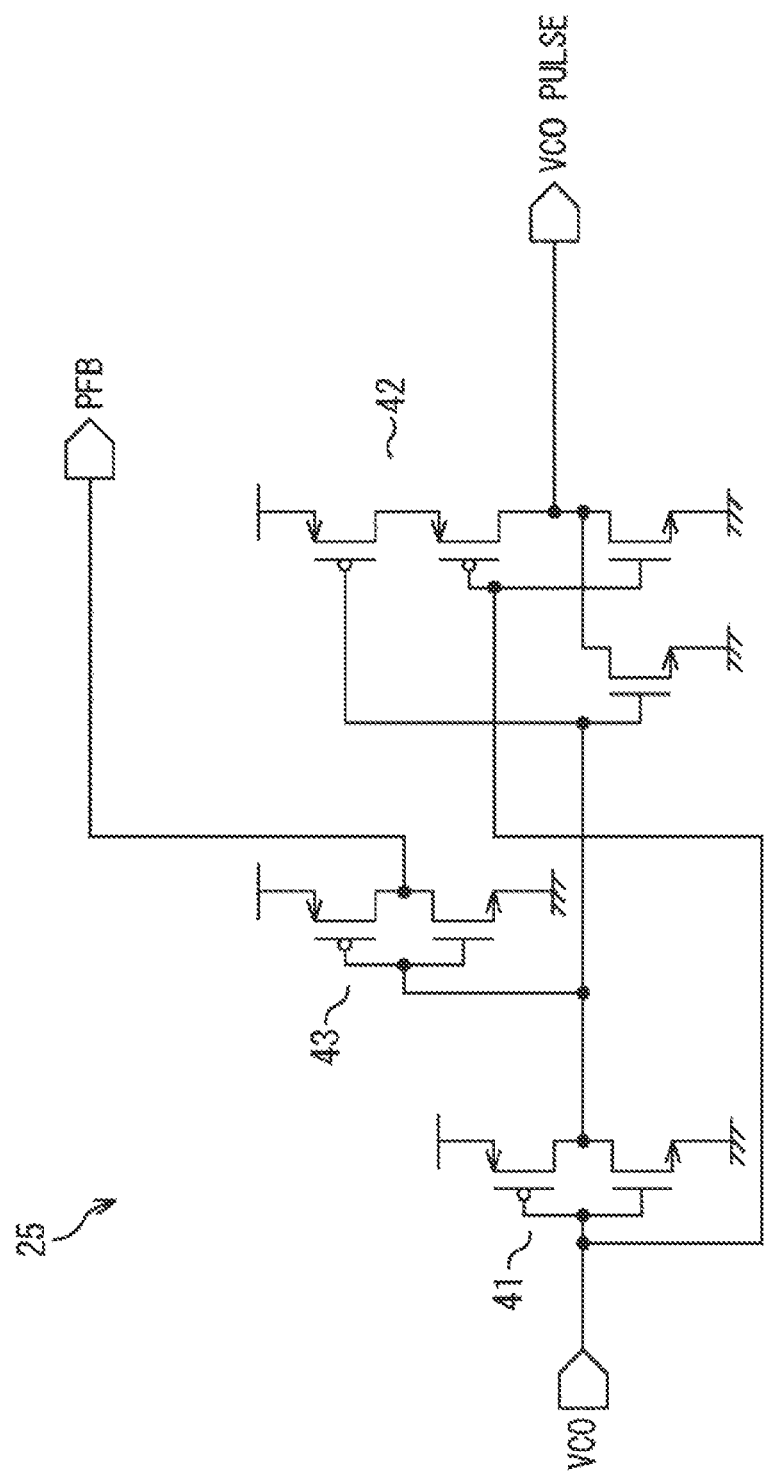
FIG. 6 is a circuit diagram depicting a configuration example of a pulse generation circuit.

FIG. 6 is a circuit diagram depicting a configuration example of a pulse generation circuit.

The pulse generation circuit 25 of FIG. 6 receives an inverted output (VCO) of the comparison circuit 22 (comparator 40) as an input signal thereto and generates a delay signal using the delay element 41 that is an inverter. Further, the pulse generation circuit 25 receives the delay signal and the inverted output of the comparator 40 to an arithmetic element 42 that is a NOR circuit as inputs thereto and generates a pulse signal (VCO PULSE). Then, as a feedback signal (PFB) for accelerating signal transition of the second stage of the comparison circuit 22, a delay signal inverted by the inversion element 43 that is an inverter is used. In particular, in the example of FIG. 6, the delay element 41 and the inversion element 43 each include an inverter, and the arithmetic element 42 includes a NOR circuit.

Figure 7:
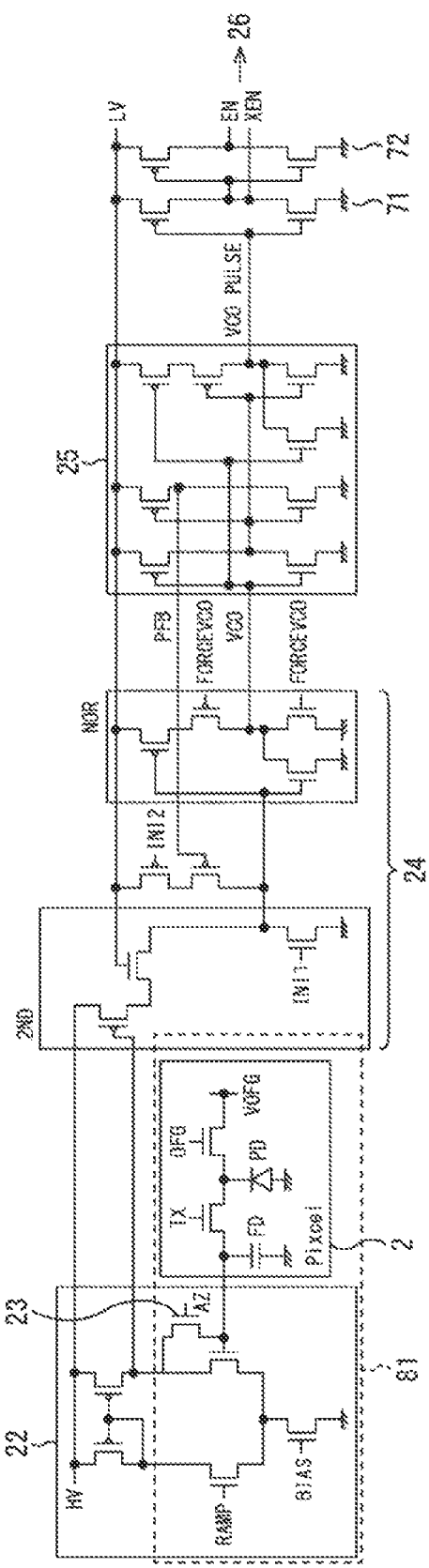
FIG. 7 is a circuit diagram depicting a configuration example of part of a solid-state imaging element to which the present technology is applied.

FIG. 7 is a circuit diagram depicting a configuration example of part of a solid-state imaging element to which the present technology is applied. It is to be noted that, in the case of the example of FIG. 7, an example of a pixel 2 that includes one PD for one FD is illustrated.

In the example of FIG. 7, as part of the solid-state imaging element 1, a pixel 2 including FD, PD, TX and OFG, a comparison circuit 22 including a differential pair of nMOS and pMOS, an AZ 23, a PFB 24 including 2ND and a NOR circuit, and inverters 71 and 72 interposed between the PFB 24 and a latch circuit 26.

In this circuit configuration, nMOS of the differential pair of the comparison circuit 22 (in the circuit of FIG. 7, an input differential pair) is an upper chip 81, and elements following nMOS are a lower chip. The upper and lower chips are connected to each other at totaling two places including each one node of the differential pair of the comparison circuit 22.

It is to be noted that the connection places of the upper and lower chips are not limited to those of the circuit of FIG. 7 but are determined from various factors such as area restriction or circuit characteristics.

Figure 8:
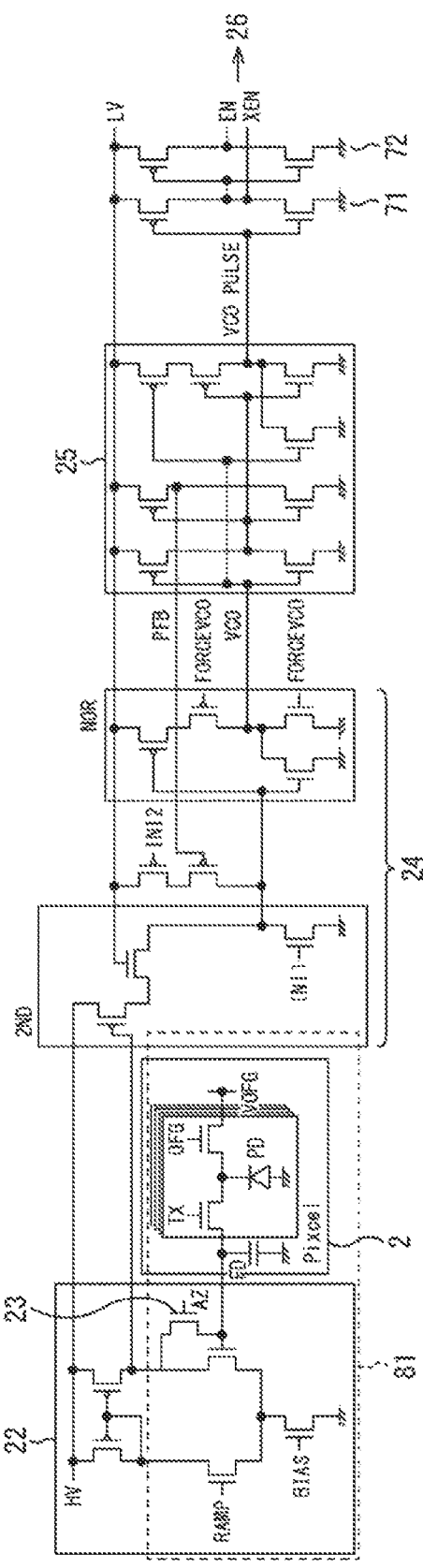
FIG. 8 is a circuit diagram depicting another configuration example of part of the solid-state imaging element to which the present technology is applied.

FIG. 8 is a circuit diagram depicting a different configuration example of part of the solid-state imaging element to which the present technology is applied. It is to be noted that, although the circuit configuration of FIG. 8 is different from that of FIG. 7 in that it has a pixel sharing configuration including four PDs for one FD, the configuration of the other part of FIG. 8 is common to the circuit configuration of FIG. 7. In other words, the present technology can be applied also to a pixel sharing configuration.

It is to be noted that the circuit configuration is not limited to any of the circuits depicted in FIGS. 7 and 8 but can be applied to a pixel AD type solid-state imaging element of any other configuration. For example, in a solid-state imaging element of the pixel AD type of a different configuration, the comparison circuit 22 including pMOS of a differential pair is adopted and, in addition, an FD is made not a component of the comparison circuit 22 but is connected through a source follower circuit. In this case, connection between the upper and lower chips is performed only at one place of the comparator and the input node of the terminal.

Figure 9:
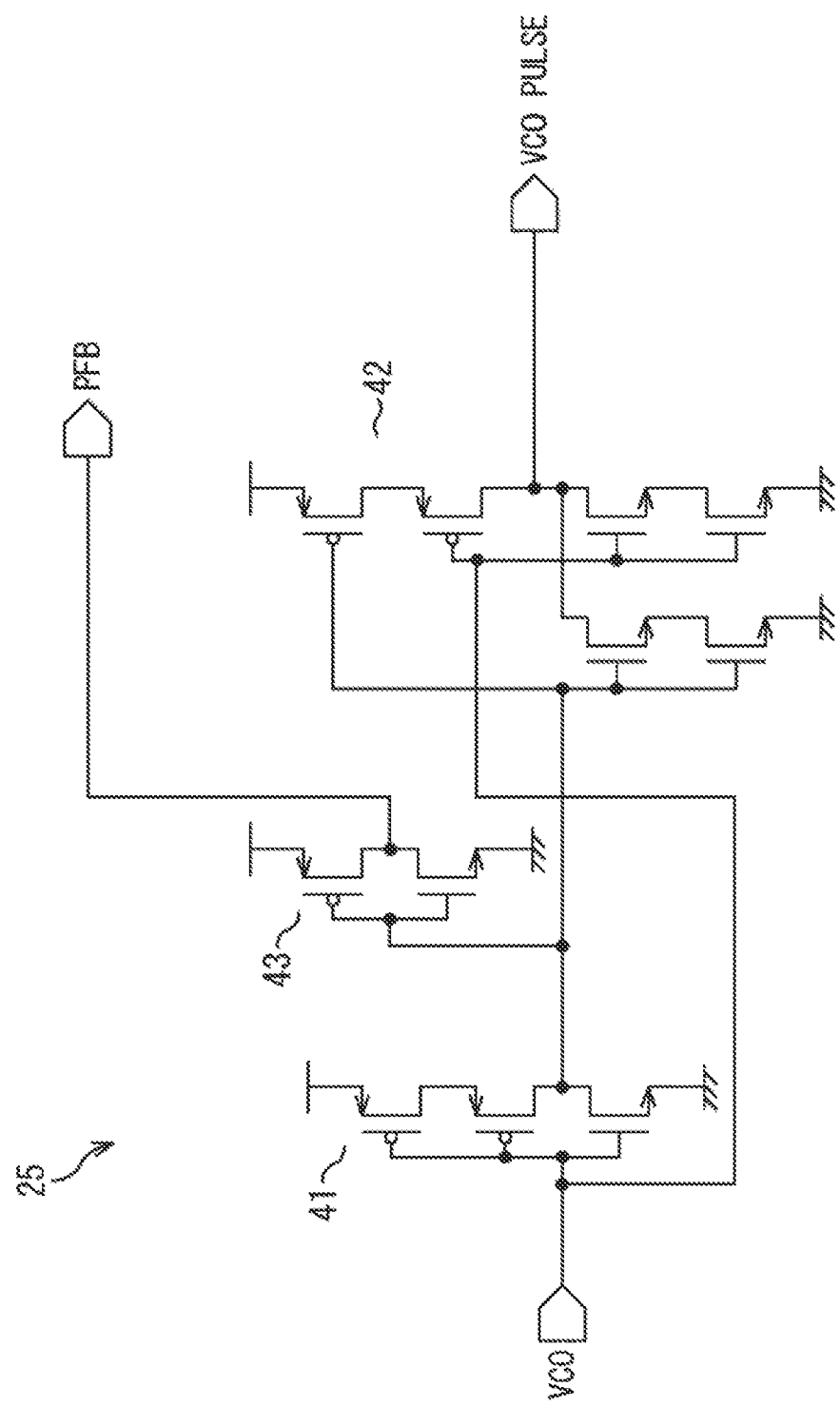
FIG. 9 is a circuit diagram depicting a different configuration example of the pulse generation circuit of FIG. 6.

FIG. 9 is a circuit diagram depicting a different configuration example of the pulse generation circuit of FIG. 6.

In the pulse generation circuit 25 of FIG. 9, the element number of transistors configuring the pulse generation circuit 25 of FIG. 6 is changed to adjust the logical threshold value of the transistors. In particular, the pulse generation circuit 25 of FIG. 9 receives an inverted output (VCO) of the comparison circuit 22 as an input thereto and generates a delay signal using the delay element 41 that is an inverter having low logic.

Further, in the pulse generation circuit 25, the delay signal and the inverted output of the comparison circuit 22 are inputted to the arithmetic element 42 that is a NOR circuit having a high logical threshold value to generate a pulse signal (VCO PULSE). Then, as the feedback signal (PFB) for accelerating signal transition in the second stage of the comparison circuit 22, a delay signal inverted by the inversion element 43 that is an inverter is used.

Figure 10:
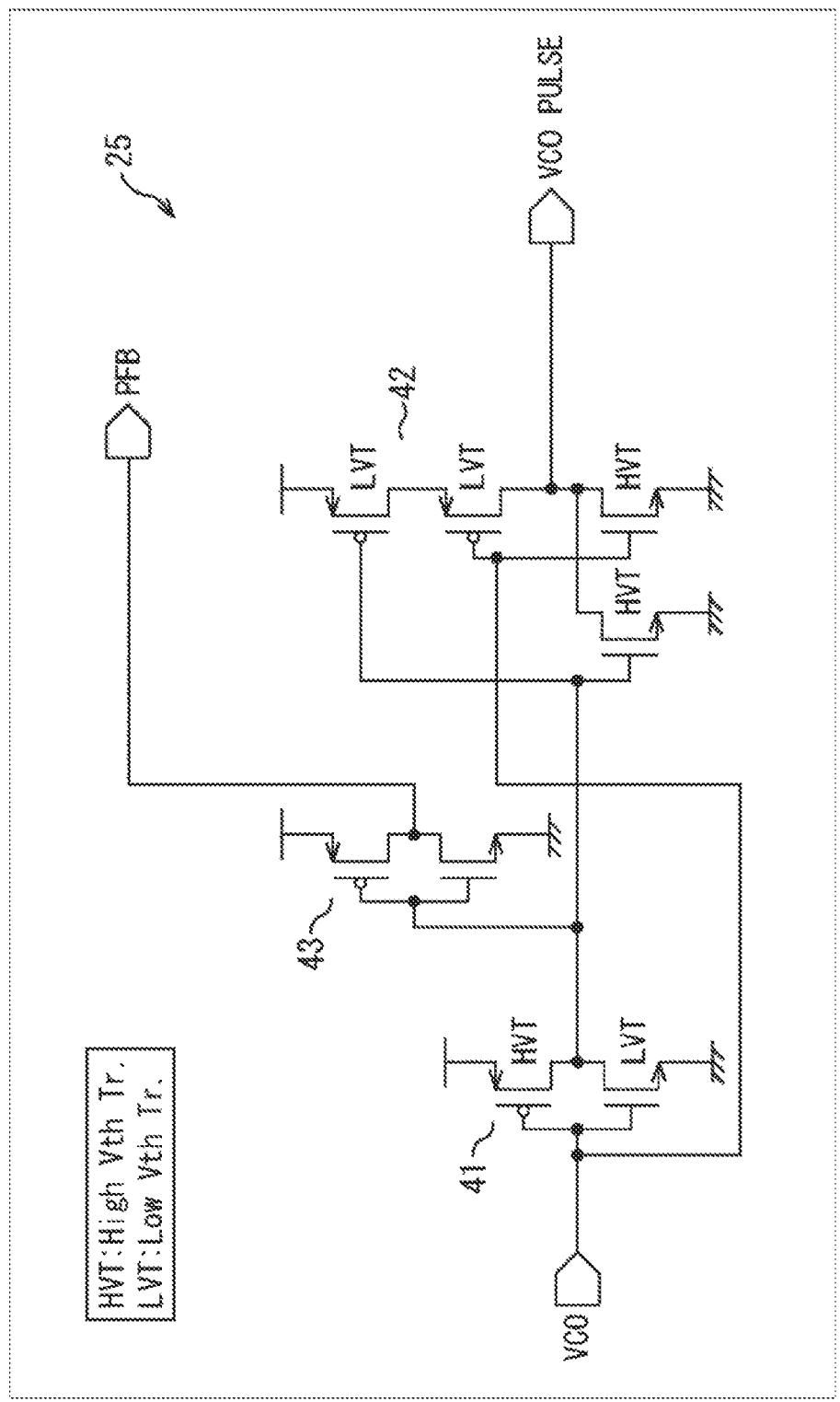
FIG. 10 is a circuit diagram depicting another different configuration example of the pulse generation circuit of FIG. 6.

FIG. 10 is a circuit diagram depicting a further configuration example of the pulse generation circuit of FIG. 6.

In the pulse generation circuit 25 of FIG. 10, the elements of the transistors configuring the pulse generation circuit 25 of FIG. 6 are changed to those having different threshold values (HVT: High Vth Tr. and LVT: Low Vth Tr.) to adjust the logical threshold value of each of the transistors. In particular, the pulse generation circuit 25 of FIG. 10 receives an inverted output (VCO) of the comparison circuit 22 as an input thereto and generates a delay signal using the delay element 41 that is an inverter having low logic.

Further, the pulse generation circuit 25 inputs the delay signal and the inverted output of the comparison circuit 22 to the arithmetic element 42 that is a NOR circuit having a high logical threshold value and generates a pulse signal (VCO PULSE). Then, as the feedback signal (PFB) for accelerating signal transition in the second stage of the comparison circuit 22, a delay signal inverted by the inversion element 43 that is an inverter is used.

Figure 11:
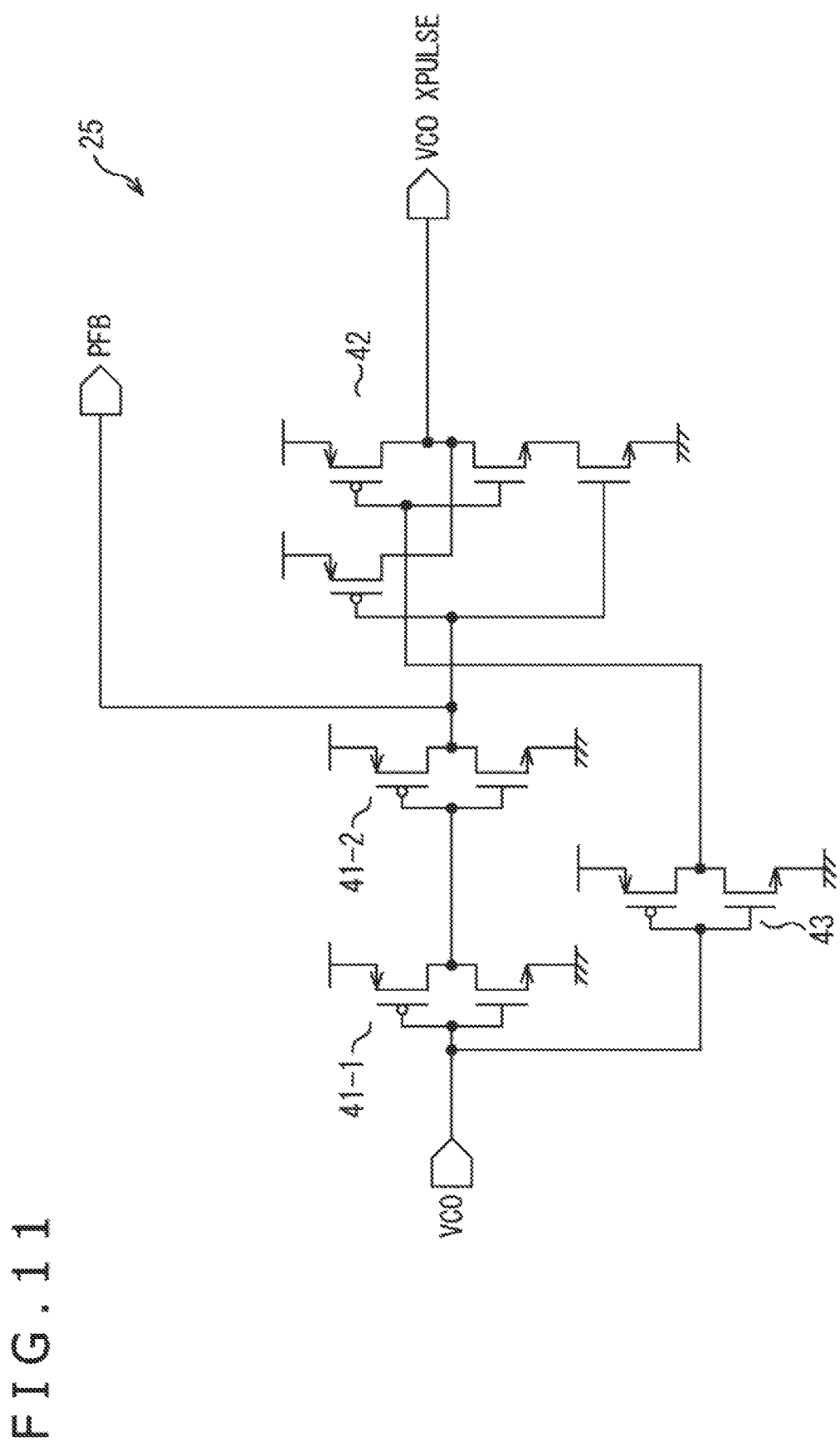
FIG. 11 is a circuit diagram depicting a configuration example of the pulse generation circuit of FIG. 6 in the case where a NAND circuit is used as an arithmetic element.

FIG. 11 is a circuit diagram depicting a configuration example of the pulse generation circuit of FIG. 6 in the case where a NAND circuit is used as the arithmetic element.

The pulse generation circuit 25 of FIG. 11 uses an arithmetic element 42 that is a NAND circuit and generates a pulse signal (VCO XPULSE) of an opposite phase to that of the pulse generation circuit 25 of FIG. 6. In particular, the pulse generation circuit 25 of FIG. 11 receives the inverted output (VCO) of the comparison circuit 22 as an input signal thereto and generates a delay signal using a delay element 41-1 and another delay element 41-2 that are inverters having low logic.

Further, in the pulse generation circuit 25, the delay signal and a signal obtained by inverting the inverted output of the comparison circuit 22 by the inversion element 43 are inputted to the arithmetic element 42 that is a NAND circuit, so that a pulse signal (VCO PULSE) is generated. Then, as the feedback signal (PFB) for accelerating signal transition in the second stage of the comparison circuit 22, a delay signal delayed by the delay element 41-1 and the delay element 41-2 is used. In particular, in the example of FIG. 11, the delay elements 41-1 and 41-2 and the inversion element 43 includes an inverter, and the arithmetic element 42 includes a NAND circuit. It is to be noted that it is necessary for the logical threshold value of the inversion element 43 to become higher than that of the delay element 41-1. This provides an effect that a time width of the pulse signal is further increased. It is to be noted that, at this time, the delay element 41-2 preferably has a high logical threshold value.

FIG. 12 is a circuit diagram depicting a configuration example of the pulse generation circuit of FIG. 9 in the case where a NAND circuit is used as the arithmetic element.

In particular, in the pulse generation circuit 25 of FIG. 12, the element number of transistors configuring the pulse generation circuit 25 of FIG. 11 is changed to adjust the logical threshold value of the transistors. In particular, the pulse generation circuit 25 of FIG. 12 receives the inverted output (VCO) of the comparison circuit 22 as an input thereto and generates a delay signal using the delay element 41-1 that is an inverter having a low logical threshold value and the delay element 41-2 that is an inverter having a high logical threshold value.

Further, the delay signal and a signal obtained by inverting the inverted output of the comparison circuit 22 by the inversion element 43 are inputted to the arithmetic element 42 that is a NAND circuit, so that a pulse signal (VCO PULSE) is generated. Then, as the feedback signal (PFB) for accelerating signal transition in the second stage of the comparison circuit 22, a delay signal delayed by the delay element 41-1 and the delay element 41-2 is used.

Figure 13:
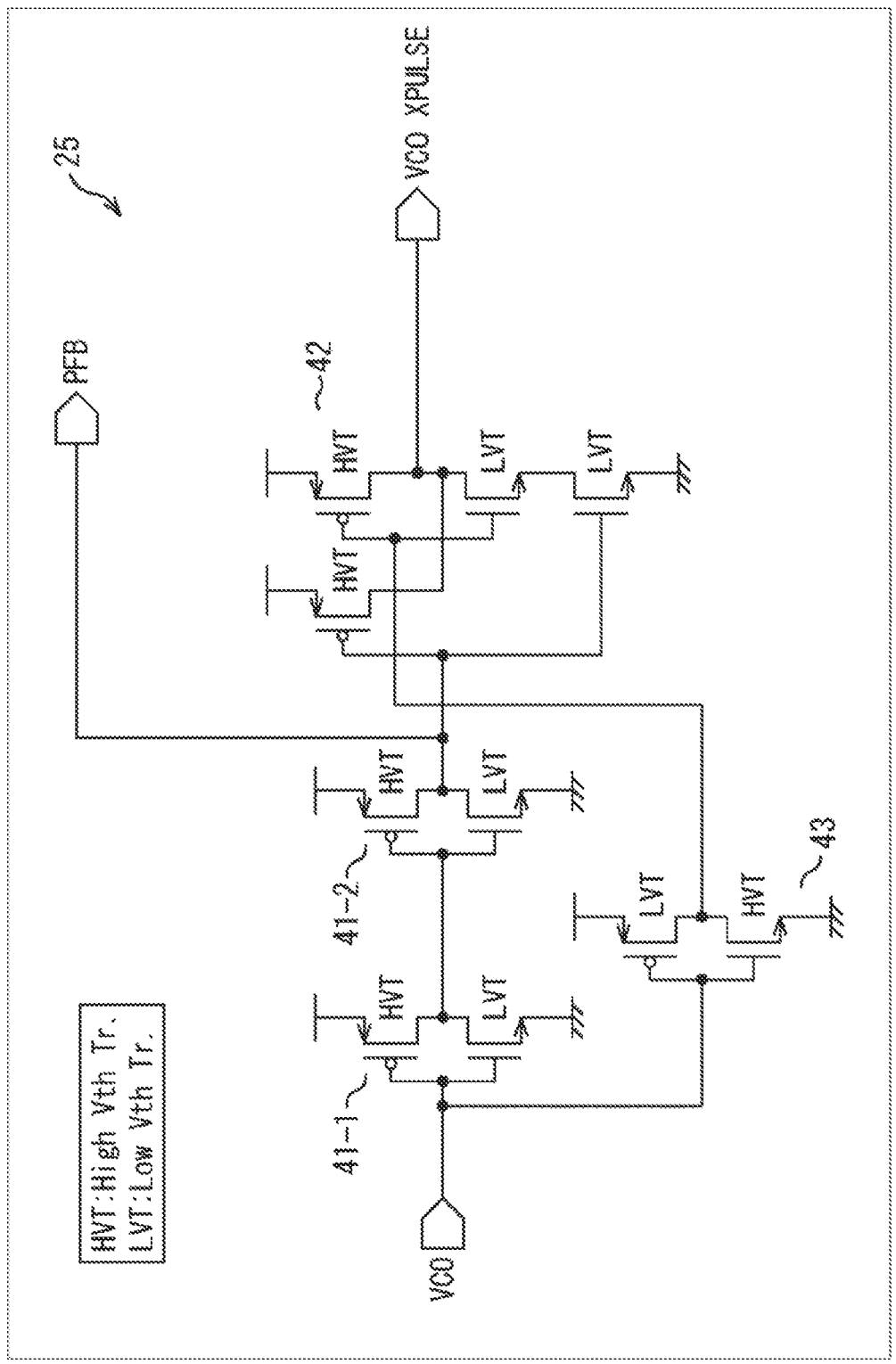
FIG. 13 is a circuit diagram depicting a configuration example of the pulse generation circuit of FIG. 10 in the case where a NAND circuit is used as an arithmetic element.

FIG. 13 is a circuit diagram depicting a configuration example of the pulse generation circuit of FIG. 10 in the case where a NAND circuit is used as the arithmetic element.

In particular, in the pulse generation circuit 25 of FIG. 13, the elements of transistors configuring the pulse generation circuit 25 of FIG. 13 are changed to those of different threshold values (HVT: High Vth Tr. and LVT: Low Vth Tr.) of the pulse generation circuit 25 of FIG. 11 to adjust the logical threshold value of the transistors. In particular, the pulse generation circuit 25 of FIG. 13 receives the inverted output (VCO) of the comparison circuit 22 as an input signal thereto and generates a delay signal using the delay element 41-1 that is an inverter having a low logical threshold value and the delay element 41-2 that is an inverter having a high logical threshold value.

Further, in the pulse generation circuit 25, the delay signal and a signal obtained by inverting the inverted output of the comparison circuit 22 by the inversion element 43 are inputted to the arithmetic element 42 that is a NAND circuit, so that a pulse signal (VCO PULSE) is generated. Then, as the feedback signal (PFB) for accelerating signal transition in the second stage of the comparison circuit 22, a delay signal delayed by the delay element 41-1 and the delay element 41-2 is used.

Figure 14:
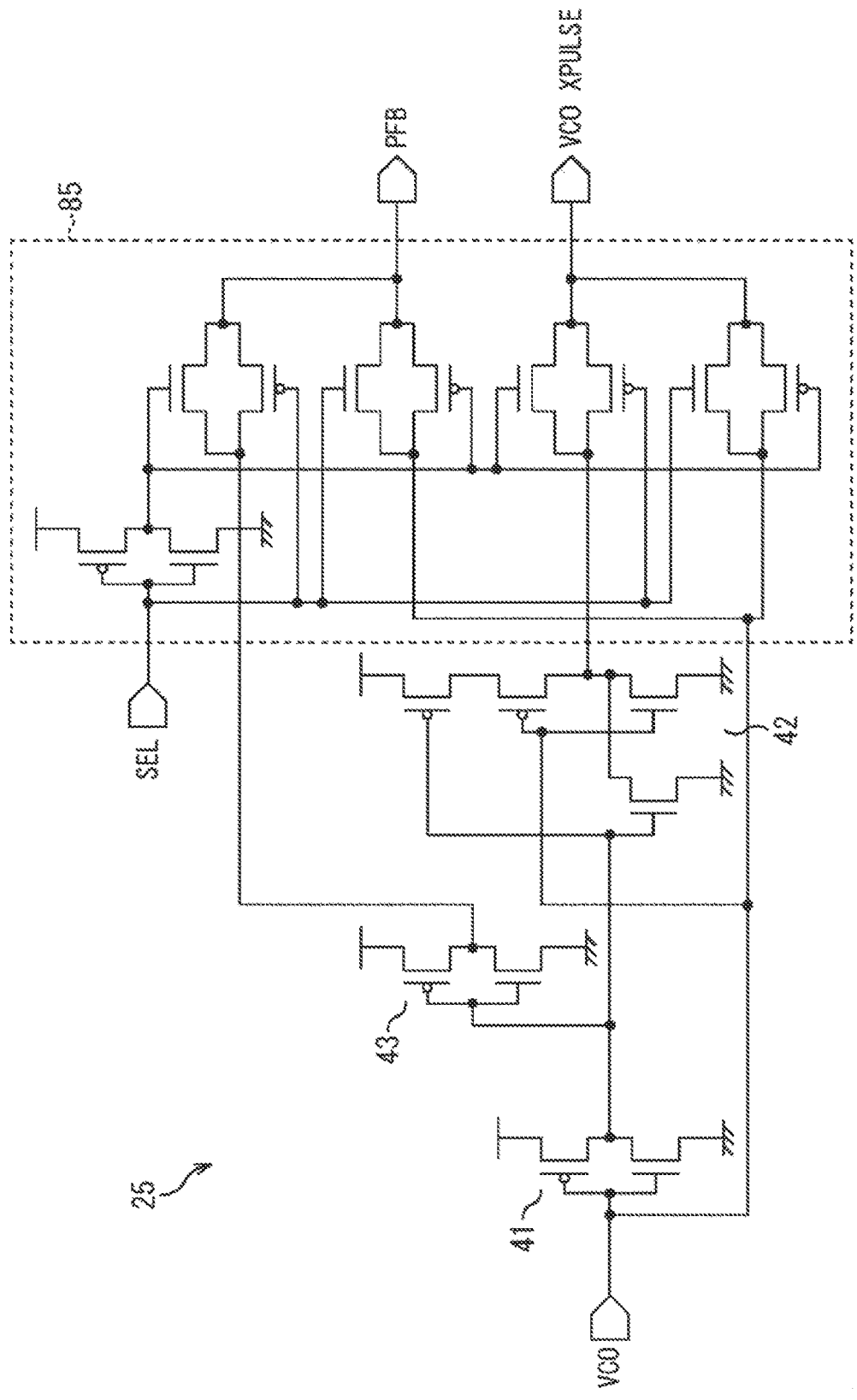
FIG. 14 is a circuit diagram depicting a configuration example of the pulse generation circuit of FIG. 6 in the case where a selector circuit is inserted.

FIG. 14 is a circuit diagram depicting a configuration example of the pulse generation circuit of FIG. 6 in the case where a selector circuit is inserted.

In the pulse generation circuit 25 of FIG. 14, a selector circuit 85 is inserted in the following stage of the arithmetic element 42 to make it possible to use a SEL signal to select a case in which the data-through period of the latch circuit 26 is controlled and in another case in which an output of the comparison circuit 22 is used directly.

By such a configuration as just described, it is possible to deal with a case in which the time width of a pulse signal cannot be secured.

Figure 15:
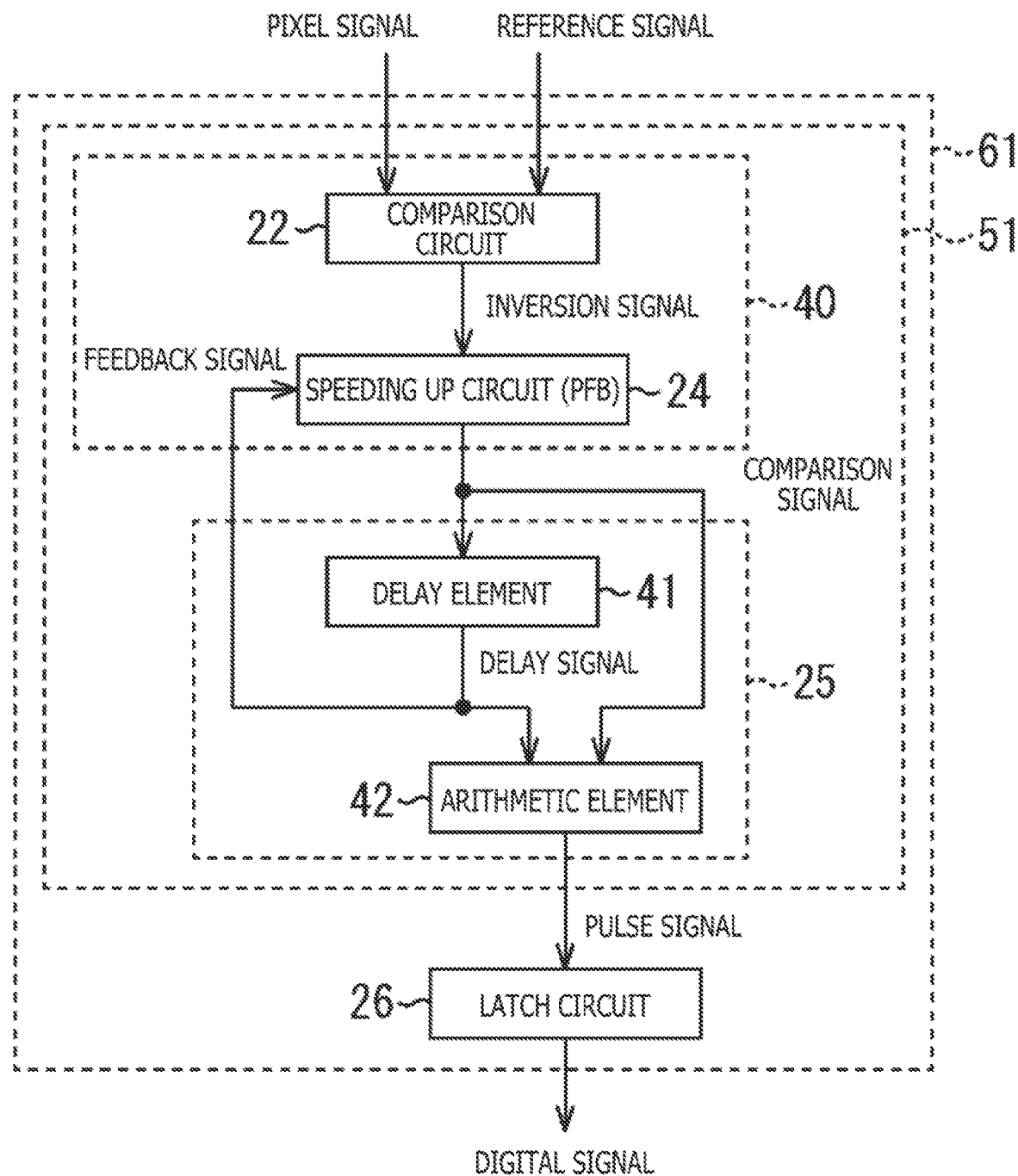
FIG. 15 is a block diagram depicting a configuration example of an AD conversion device to which the present technology is applied.

FIG. 15 is a block diagram depicting a configuration example of an AD conversion device to which the present technology is applied.

The CIS of the pixel AD method has such premises that the area restriction is severe, that an AD conversion device is disposed for each pixel, and that a circuit of a small area is preferable.

In the AD conversion device 61 of FIG. 15, for the object of implementing a small area circuit, a PFB 24 that is a speeding up circuit is adopted in the comparator 40 in order to accelerate signal transition in the comparison circuit 22 (comparator 40). The PFB 24 requires a feedback signal. Although a comparison signal has been used as the feedback signal in the past, in the present technology, a delay signal is used as the feedback signal. By this, the acceleration timing of signal transition is delayed. Accordingly, a period within which the signal transition is comparatively gentle is provided. In the pulse generation circuit 25 for controlling the data-through period of the latch circuit 26, by the provision of the delay element 41 within this period, a delay signal is generated at the high and low levels of the logical threshold value. Then, a pulse signal is generated through the arithmetic element 42 from the delay signal and the comparison signal. Effects expected from this are such as described below.

1. The time width of a pulse signal can be secured sufficiently.
2. The pulse generation circuit can be formed with a small area.
3. Reduction in power consumption can be anticipated by data-through period control.

Figure 16:
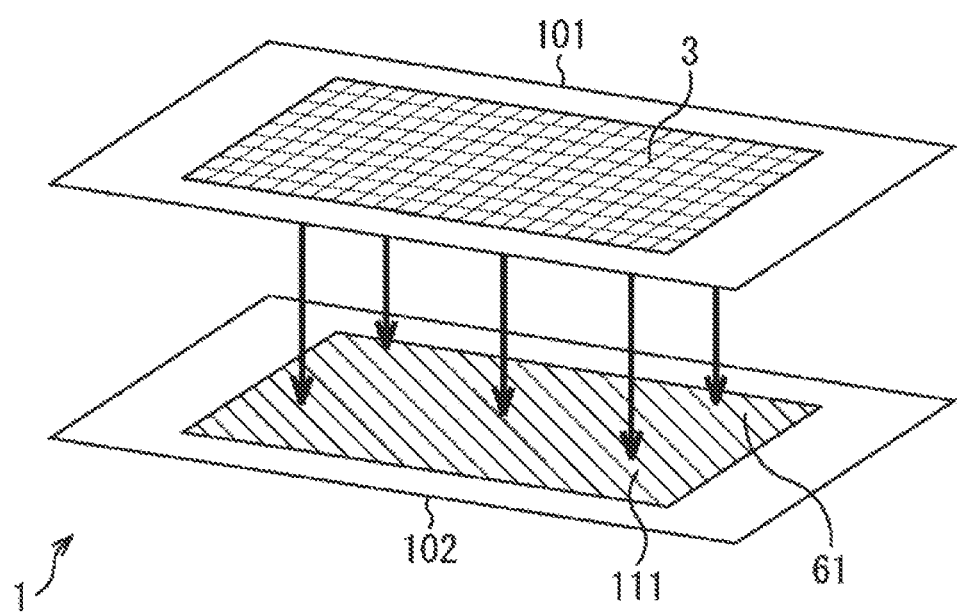
FIG. 16 is a process chart of a fabrication process of a solid-state imaging element.

FIG. 16 is a view depicting a configuration example of a solid-state imaging element of the pixel AD type.

In the solid-state imaging element 1 of FIG. 16, a pixel region 3 is mounted on an upper chip 101, and an AD conversion device 61 and a logic circuit 111 are mounted on a lower chip 102, and the upper chip 101 and the lower chip 102 are stacked using a Cu—Cu joining technology or the like. Since one AD conversion device 61 corresponds to one pixel, a contact between the upper and lower chips is provided for each pixel. It is to be noted that the number of stacked layers is not limited to two layers and may be any number as long as it is equal to or greater than 2.

2. Example of Use of Image Sensor

Figure 17:
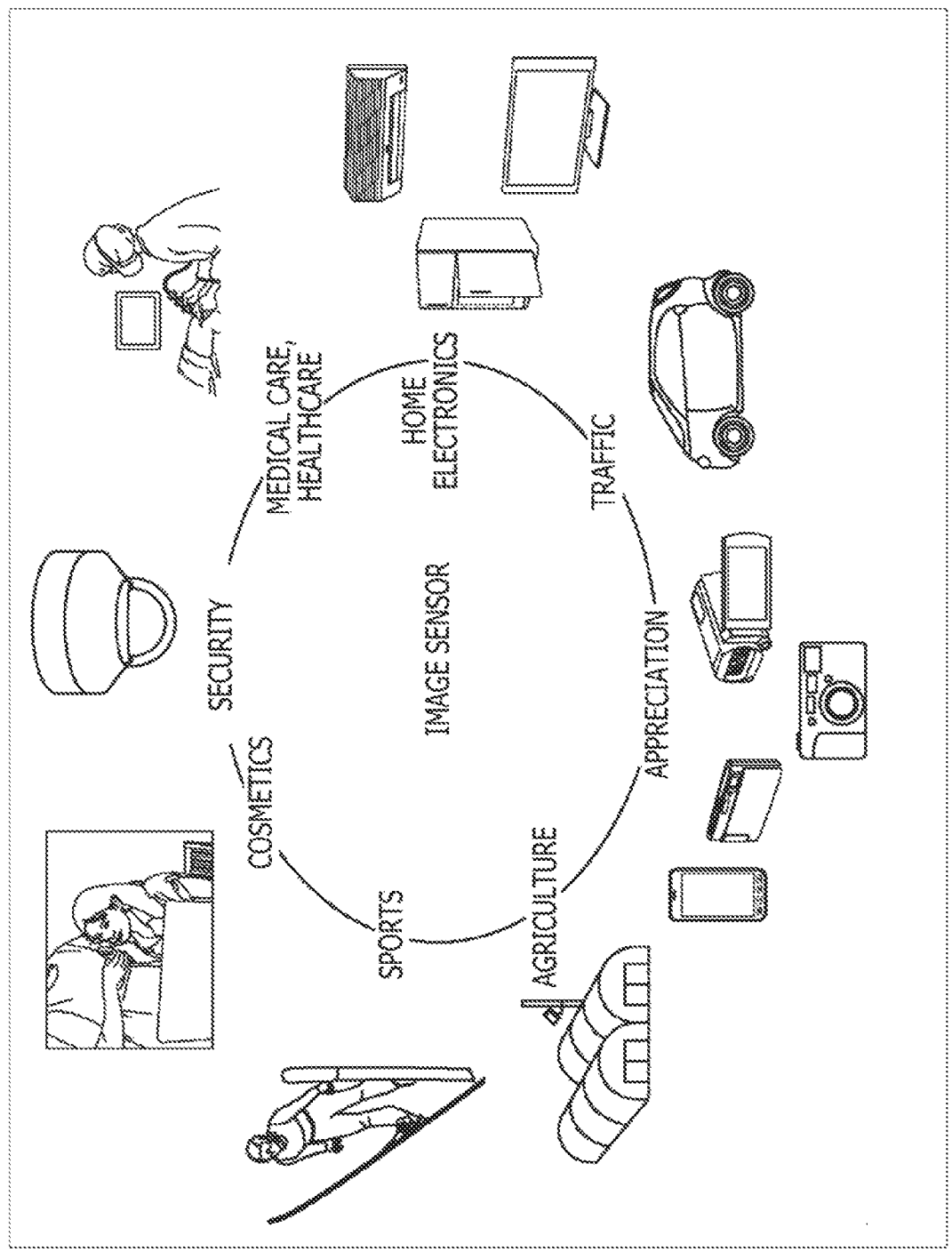
FIG. 17 is a view depicting an example of use of an image sensor to which the present technology is applied.

FIG. 17 is a view depicting an example of use in which the solid-state imaging element described above is used.

The solid-state imaging element (image sensor) described above can be used in various cases in which light such as visible light, infrared light, ultraviolet light, or an X ray is sensed, for example, in the following manner.

An apparatus for imaging an image to be provided for appreciation such as a digital camera or portable equipment with a camera function An apparatus used for traffic such as a vehicle-carried sensor for imaging forwardly or rearwardly, around or within an automobile for the object of safe driving such as automatic stopping or recognition of a state of the driver, a surveillance camera for monitoring a traveling vehicle or a road, a distance measurement sensor for measuring the distance between vehicles or the like An apparatus used in household appliances such as a TV set, a refrigerator or an air conditioner for imaging a gesture of a user and performing an apparatus operation in accordance with the gesture An apparatus for medical use or healthcare use such as an endoscope or a device for imaging a blood vessel by reception of infrared light An apparatus for security use such as a surveillance camera for a security application or a camera for a personal authentication application An apparatus for cosmetic use such as a skin measuring instrument for imaging the skin or a microscope for imaging the scalp An apparatus for sports use such as an action camera or a wearable camera for a sports application or the like An apparatus for agricultural use such as a camera for monitoring the state of fields and crops 3. Example of Electronic Equipment <Configuration Example of Electronic Equipment>

Further, the present technology is not restricted to application to a solid-state imaging element but can be applied also to an imaging apparatus. Here, the imaging apparatus signifies electronic equipment having an imaging function such as a camera system of a digital still camera or a digital video camera or a mobile phone. It is to be noted that the imaging apparatus may be in the form of a module incorporated in electronic equipment, namely, a camera module.

Here, a configuration example of electronic equipment of the present technology is described with reference to FIG. 18.

Figure 18:
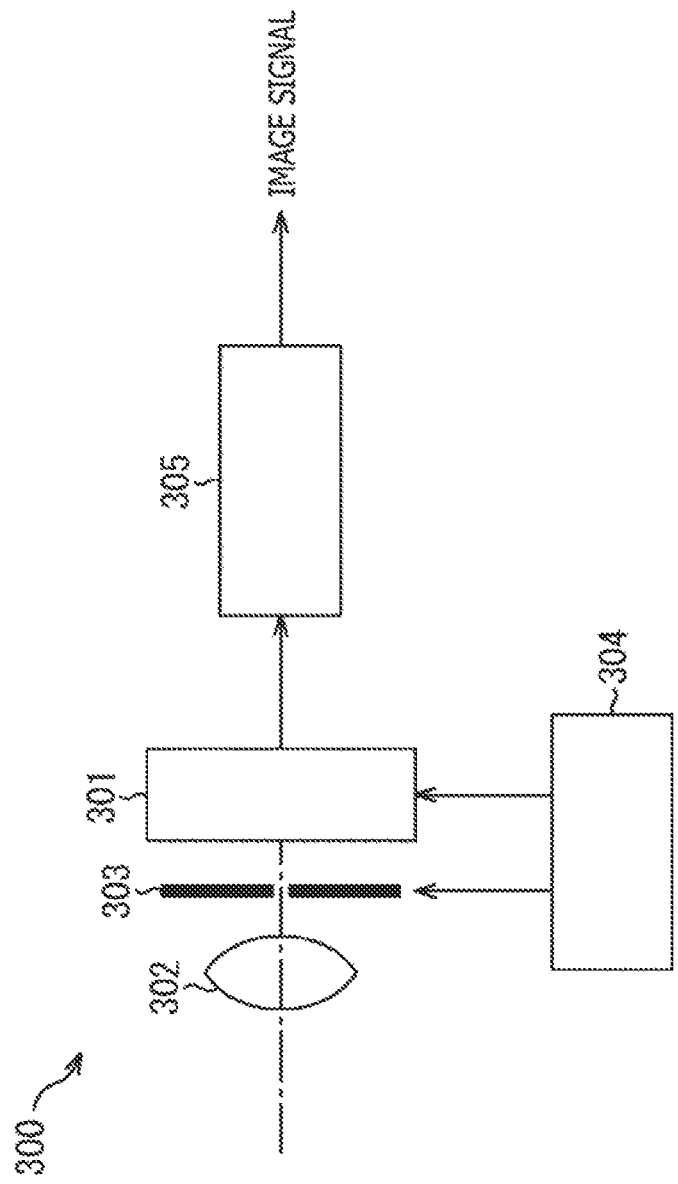
FIG. 18 is a block diagram depicting a configuration example of electronic equipment to which the present technology is applied.

The electronic equipment 300 depicted in FIG. 18 includes a solid-state imaging element (device chip) 301, an optical lens 302, a shutter device 303, a driving circuit 304, and a signal processing circuit 305. As the solid-state imaging element 301, the solid-state imaging element 1 of the present technology described hereinabove is provided.

The optical lens 302 forms an image of image light (incident light) from an imaging object on an imaging plane of the solid-state imaging element 301. Consequently, signal charge is accumulated for a fixed period into the solid-state imaging element 301. The shutter device 303 controls a light irradiation period and a light blocking period for the solid-state imaging element 301.

The driving circuit 304 supplies driving signals for controlling a signal transfer operation of the solid-state imaging element 301, a shutter operation of the shutter device 303, and a light emission operation of a light emitting section not depicted. The driving circuit 304 controls various operations using parameters set by a CPU not depicted. The solid-state imaging element 301 performs signal transfer in response to a driving signal (timing signal) supplied from the driving circuit 304. The signal processing circuit 305 performs various signal processes for a signal outputted from the solid-state imaging element 301. An image signal for which the signal processes have been performed is stored into a storage medium such as a memory or outputted to a monitor.

4. Application Example to In-Vivo Information Acquisition System

The technology according to the present disclosure (present technology) can be applied to various products. For example, the technology according to the present disclosure may be applied to an endoscopic surgery system.

Figure 19:
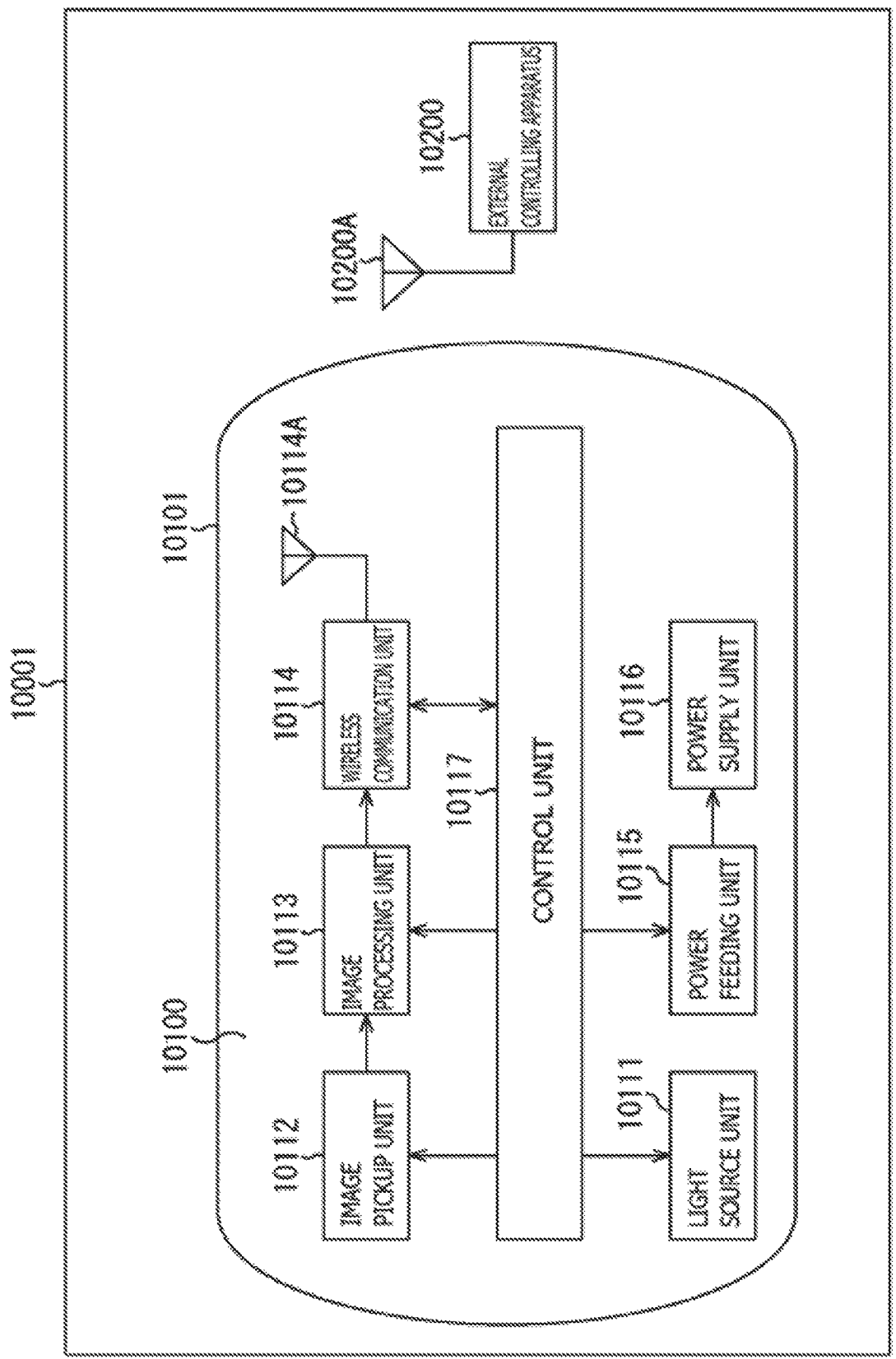
FIG. 19 is a block diagram depicting an example of a schematic configuration of an in-vivo information acquisition system.

FIG. 19 is a block diagram depicting an example of a schematic configuration of an in-vivo information acquisition system of a patient using a capsule type endoscope, to which the technology according to an embodiment of the present disclosure (present technology) can be applied.

The in-vivo information acquisition system 10001 includes a capsule type endoscope 10100 and an external controlling apparatus 10200.

The capsule type endoscope 10100 is swallowed by a patient at the time of inspection. The capsule type endoscope 10100 has an image pickup function and a wireless communication function and successively picks up an image of the inside of an organ such as the stomach or an intestine (hereinafter referred to as in-vivo image) at predetermined intervals while it moves inside of the organ by peristaltic motion for a period of time until it is naturally discharged from the patient. Then, the capsule type endoscope 10100 successively transmits information of the in-vivo image to the external controlling apparatus 10200 outside the body by wireless transmission.

The external controlling apparatus 10200 integrally controls operation of the in-vivo information acquisition system 10001. Further, the external controlling apparatus 10200 receives information of an in-vivo image transmitted thereto from the capsule type endoscope 10100 and generates image data for displaying the in-vivo image on a display apparatus (not depicted) on the basis of the received information of the in-vivo image.

In the in-vivo information acquisition system 10001, an in-vivo image imaged a state of the inside of the body of a patient can be acquired at any time in this manner for a period of time until the capsule type endoscope 10100 is discharged after it is swallowed.

A configuration and functions of the capsule type endoscope 10100 and the external controlling apparatus 10200 are described in more detail below.

The capsule type endoscope 10100 includes a housing 10101 of the capsule type, in which a light source unit 10111, an image pickup unit 10112, an image processing unit 10113, a wireless communication unit 10114, a power feeding unit 10115, a power supply unit 10116 and a control unit 10117 are accommodated.

The light source unit 10111 includes a light source such as, for example, a light emitting diode (LED) and irradiates light on an image pickup field-of-view of the image pickup unit 10112.

The image pickup unit 10112 includes an image pickup element and an optical system including a plurality of lenses provided at a preceding stage to the image pickup element. Reflected light (hereinafter referred to as observation light) of light irradiated on a body tissue which is an observation target is condensed by the optical system and introduced into the image pickup element. In the image pickup unit 10112, the incident observation light is photoelectrically converted by the image pickup element, by which an image signal corresponding to the observation light is generated. The image signal generated by the image pickup unit 10112 is provided to the image processing unit 10113.

The image processing unit 10113 includes a processor such as a central processing unit (CPU) or a graphics processing unit (GPU) and performs various signal processes for an image signal generated by the image pickup unit 10112. The image processing unit 10113 provides the image signal for which the signal processes have been performed thereby as RAW data to the wireless communication unit 10114.

The wireless communication unit 10114 performs a predetermined process such as a modulation process for the image signal for which the signal processes have been performed by the image processing unit 10113 and transmits the resulting image signal to the external controlling apparatus 10200 through an antenna 10114A. Further, the wireless communication unit 10114 receives a control signal relating to driving control of the capsule type endoscope 10100 from the external controlling apparatus 10200 through the antenna 10114A. The wireless communication unit 10114 provides the control signal received from the external controlling apparatus 10200 to the control unit 10117.

The power feeding unit 10115 includes an antenna coil for power reception, a power regeneration circuit for regenerating electric power from current generated in the antenna coil, a voltage booster circuit and so forth. The power feeding unit 10115 generates electric power using the principle of non-contact charging.

The power supply unit 10116 includes a secondary battery and stores electric power generated by the power feeding unit 10115. In FIG. 19, in order to avoid complicated illustration, an arrow mark indicative of a supply destination of electric power from the power supply unit 10116 and so forth are omitted. However, electric power stored in the power supply unit 10116 is supplied to and can be used to drive the light source unit 10111, the image pickup unit 10112, the image processing unit 10113, the wireless communication unit 10114 and the control unit 10117.

The control unit 10117 includes a processor such as a CPU and suitably controls driving of the light source unit 10111, the image pickup unit 10112, the image processing unit 10113, the wireless communication unit 10114 and the power feeding unit 10115 in accordance with a control signal transmitted thereto from the external controlling apparatus 10200.

The external controlling apparatus 10200 includes a processor such as a CPU or a GPU, a microcomputer, a control board or the like in which a processor and a storage element such as a memory are mixedly incorporated. The external controlling apparatus 10200 transmits a control signal to the control unit 10117 of the capsule type endoscope 10100 through an antenna 10200A to control operation of the capsule type endoscope 10100. In the capsule type endoscope 10100, an irradiation condition of light upon an observation target of the light source unit 10111 can be changed, for example, in accordance with a control signal from the external controlling apparatus 10200. Further, an image pickup condition (for example, a frame rate, an exposure value or the like of the image pickup unit 10112) can be changed in accordance with a control signal from the external controlling apparatus 10200. Further, the substance of processing by the image processing unit 10113 or a condition for transmitting an image signal from the wireless communication unit 10114 (for example, a transmission interval, a transmission image number or the like) may be changed in accordance with a control signal from the external controlling apparatus 10200.

Further, the external controlling apparatus 10200 performs various image processes for an image signal transmitted thereto from the capsule type endoscope 10100 to generate image data for displaying a picked up in-vivo image on the display apparatus. As the image processes, various signal processes can be performed such as, for example, a development process (demosaic process), an image quality improving process (bandwidth enhancement process, a super-resolution process, a noise reduction (NR) process and/or image stabilization process) and/or an enlargement process (electronic zooming process). The external controlling apparatus 10200 controls driving of the display apparatus to cause the display apparatus to display a picked up in-vivo image on the basis of generated image data. Alternatively, the external controlling apparatus 10200 may also control a recording apparatus (not depicted) to record generated image data or control a printing apparatus (not depicted) to output generated image data by printing.

An example of an in-vivo information acquisition system to which the technology according to the present disclosure can be applied has been described. The technology according to the present disclosure can be applied to the image pickup unit 10112 from within the configuration described hereinabove. In particular, for example, the solid-state imaging element 1 of FIG. 16 can be applied to the image pickup unit 10112. By applying the technology according to the present disclosure to the image pickup unit 10112, the time width of a pulse signal can be secured sufficiently, and the pixel size can be reduced. Accordingly, it is possible to downsize the apparatus, for example. Further, reduction in power consumption can be anticipated.

5. Application Example to Endoscopic Surgery System

The technology according to the present disclosure (present technology) can be applied to various products. For example, the technology according to the present disclosure may be applied to an endoscopic surgery system.

Figure 20:
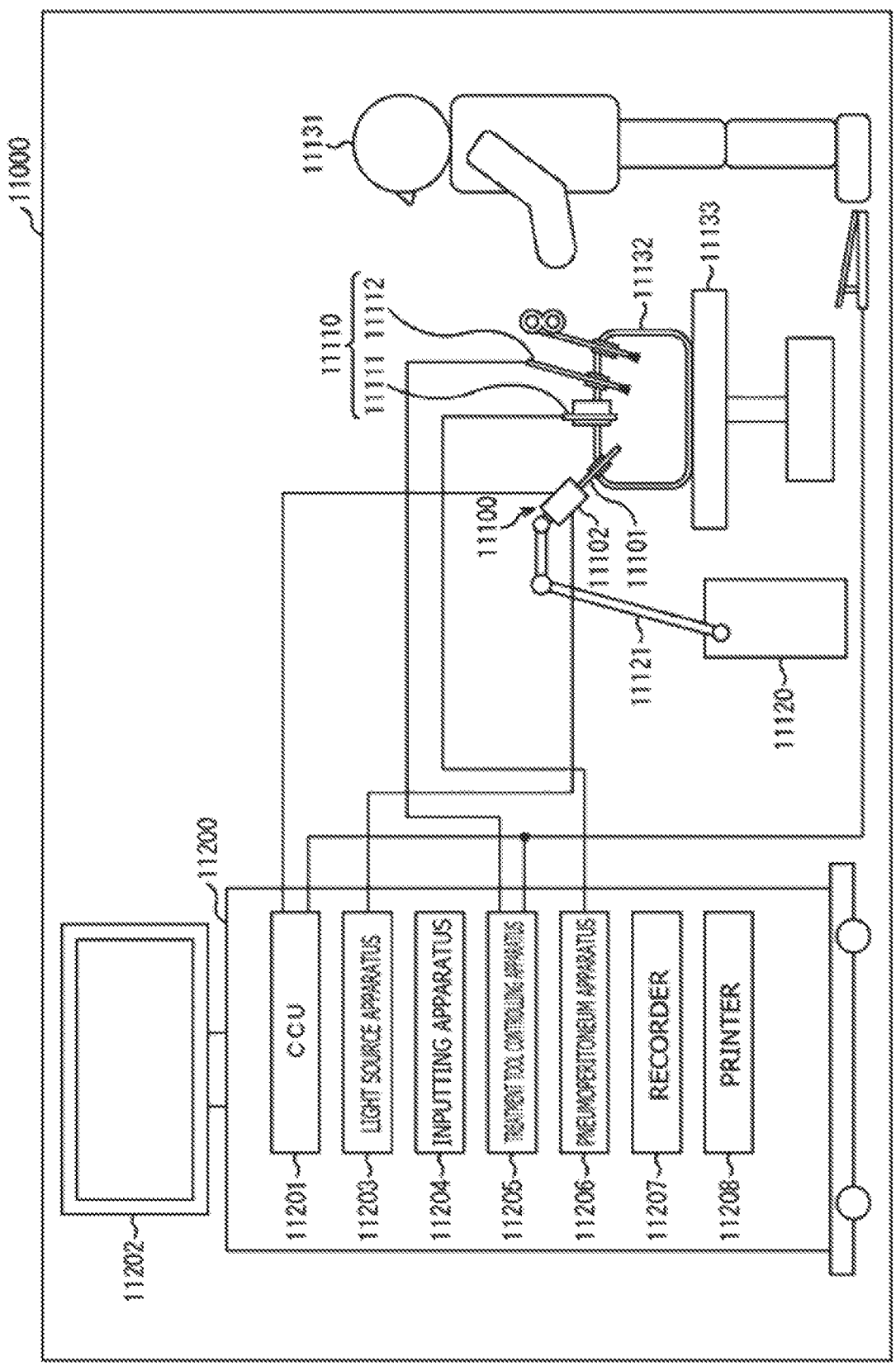
FIG. 20 is a view depicting an example of a schematic configuration of an endoscopic surgery system.

FIG. 20 is a view depicting an example of a schematic configuration of an endoscopic surgery system to which the technology according to an embodiment of the present disclosure (present technology) can be applied.

In FIG. 20, a state is illustrated in which a surgeon (medical doctor) 11131 is using an endoscopic surgery system 11000 to perform surgery for a patient 11132 on a patient bed 11133. As depicted, the endoscopic surgery system 11000 includes an endoscope 11100, other surgical tools 11110 such as a pneumoperitoneum tube 11111 and an energy device 11112, a supporting arm apparatus 11120 which supports the endoscope 11100 thereon, and a cart 11200 on which various apparatus for endoscopic surgery are mounted.

The endoscope 11100 includes a lens barrel 11101 having a region of a predetermined length from a distal end thereof to be inserted into a body cavity of the patient 11132, and a camera head 11102 connected to a proximal end of the lens barrel 11101. In the example depicted, the endoscope 11100 is depicted which includes as a rigid endoscope having the lens barrel 11101 of the hard type. However, the endoscope 11100 may otherwise be included as a flexible endoscope having the lens barrel 11101 of the flexible type.

The lens barrel 11101 has, at a distal end thereof, an opening in which an objective lens is fitted. A light source apparatus 11203 is connected to the endoscope 11100 such that light generated by the light source apparatus 11203 is introduced to a distal end of the lens barrel 11101 by a light guide extending in the inside of the lens barrel 11101 and is irradiated toward an observation target in a body cavity of the patient 11132 through the objective lens. It is to be noted that the endoscope 11100 may be a forward-viewing endoscope or may be an oblique-viewing endoscope or a side-viewing endoscope.

An optical system and an image pickup element are provided in the inside of the camera head 11102 such that reflected light (observation light) from the observation target is condensed on the image pickup element by the optical system. The observation light is photo-electrically converted by the image pickup element to generate an electric signal corresponding to the observation light, namely, an image signal corresponding to an observation image. The image signal is transmitted as RAW data to a CCU 11201.

The CCU 11201 includes a central processing unit (CPU), a graphics processing unit (GPU) or the like and integrally controls operation of the endoscope 11100 and a display apparatus 11202. Further, the CCU 11201 receives an image signal from the camera head 11102 and performs, for the image signal, various image processes for displaying an image based on the image signal such as, for example, a development process (demosaic process).

The display apparatus 11202 displays thereon an image based on an image signal, for which the image processes have been performed by the CCU 11201, under the control of the CCU 11201.

The light source apparatus 11203 includes a light source such as, for example, a light emitting diode (LED) and supplies irradiation light upon imaging of a surgical region to the endoscope 11100.

An inputting apparatus 11204 is an input interface for the endoscopic surgery system 11000. A user can perform inputting of various kinds of information or instruction inputting to the endoscopic surgery system 11000 through the inputting apparatus 11204. For example, the user would input an instruction or a like to change an image pickup condition (type of irradiation light, magnification, focal distance or the like) by the endoscope 11100.

A treatment tool controlling apparatus 11205 controls driving of the energy device 11112 for cautery or incision of a tissue, sealing of a blood vessel or the like. A pneumoperitoneum apparatus 11206 feeds gas into a body cavity of the patient 11132 through the pneumoperitoneum tube 11111 to inflate the body cavity in order to secure the field of view of the endoscope 11100 and secure the working space for the surgeon. A recorder 11207 is an apparatus capable of recording various kinds of information relating to surgery. A printer 11208 is an apparatus capable of printing various kinds of information relating to surgery in various forms such as a text, an image or a graph.

It is to be noted that the light source apparatus 11203 which supplies irradiation light when a surgical region is to be imaged to the endoscope 11100 may include a white light source which includes, for example, an LED, a laser light source or a combination of them. Where a white light source includes a combination of red, green, and blue (RGB) laser light sources, since the output intensity and the output timing can be controlled with a high degree of accuracy for each color (each wavelength), adjustment of the white balance of a picked up image can be performed by the light source apparatus 11203. Further, in this case, if laser beams from the respective RGB laser light sources are irradiated time-divisionally on an observation target and driving of the image pickup elements of the camera head 11102 are controlled in synchronism with the irradiation timings. Then images individually corresponding to the R, G and B colors can be also picked up time-divisionally. According to this method, a color image can be obtained even if color filters are not provided for the image pickup element.

Further, the light source apparatus 11203 may be controlled such that the intensity of light to be outputted is changed for each predetermined time. By controlling driving of the image pickup element of the camera head 11102 in synchronism with the timing of the change of the intensity of light to acquire images time-divisionally and synthesizing the images, an image of a high dynamic range free from underexposed blocked up shadows and overexposed highlights can be created.

Further, the light source apparatus 11203 may be configured to supply light of a predetermined wavelength band ready for special light observation. In special light observation, for example, by utilizing the wavelength dependency of absorption of light in a body tissue to irradiate light of a narrow band in comparison with irradiation light upon ordinary observation (namely, white light), narrow band observation (narrow band imaging) of imaging a predetermined tissue such as a blood vessel of a superficial portion of the mucous membrane or the like in a high contrast is performed. Alternatively, in special light observation, fluorescent observation for obtaining an image from fluorescent light generated by irradiation of excitation light may be performed. In fluorescent observation, it is possible to perform observation of fluorescent light from a body tissue by irradiating excitation light on the body tissue (autofluorescence observation) or to obtain a fluorescent light image by locally injecting a reagent such as indocyanine green (ICG) into a body tissue and irradiating excitation light corresponding to a fluorescent light wavelength of the reagent upon the body tissue. The light source apparatus 11203 can be configured to supply such narrow-band light and/or excitation light suitable for special light observation as described above.

Figure 21:
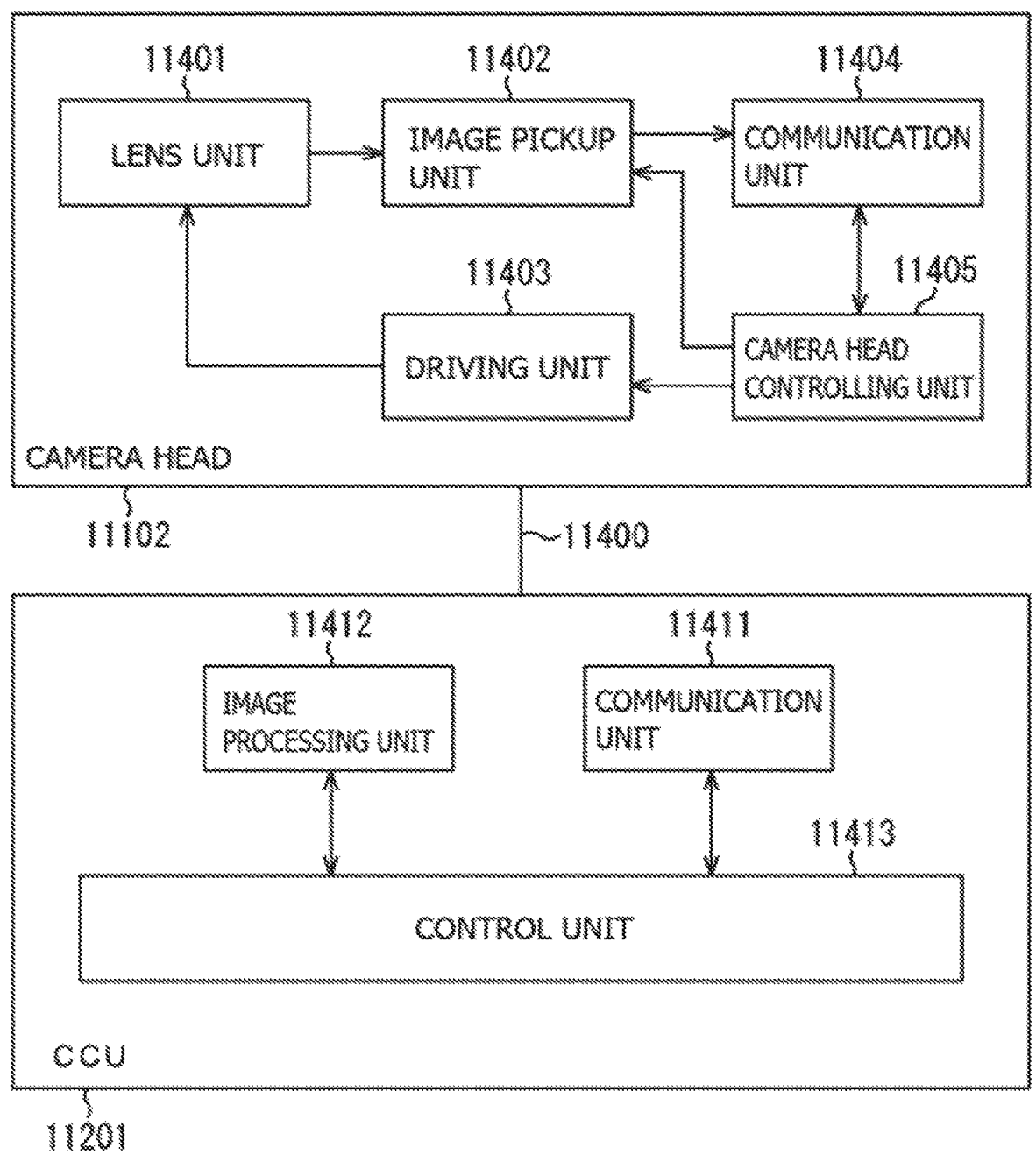
FIG. 21 is a block diagram depicting an example of a functional configuration of a camera head and a camera control unit (CCU).

FIG. 21 is a block diagram depicting an example of a functional configuration of the camera head 11102 and the CCU 11201 depicted in FIG. 20.

The camera head 11102 includes a lens unit 11401, an image pickup unit 11402, a driving unit 11403, a communication unit 11404 and a camera head controlling unit 11405. The CCU 11201 includes a communication unit 11411, an image processing unit 11412 and a control unit 11413. The camera head 11102 and the CCU 11201 are connected for communication to each other by a transmission cable 11400.

The lens unit 11401 is an optical system, provided at a connecting location to the lens barrel 11101. Observation light taken in from a distal end of the lens barrel 11101 is guided to the camera head 11102 and introduced into the lens unit 11401. The lens unit 11401 includes a combination of a plurality of lenses including a zoom lens and a focusing lens.

The number of image pickup elements which is included by the image pickup unit 11402 may be one (single-plate type) or a plural number (multi-plate type). Where the image pickup unit 11402 is configured as that of the multi-plate type, for example, image signals corresponding to respective R, G and B are generated by the image pickup elements, and the image signals may be synthesized to obtain a color image. The image pickup unit 11402 may also be configured so as to have a pair of image pickup elements for acquiring respective image signals for the right eye and the left eye ready for three dimensional (3D) display. If 3D display is performed, then the depth of a living body tissue in a surgical region can be comprehended more accurately by the surgeon 11131. It is to be noted that, where the image pickup unit 11402 is configured as that of stereoscopic type, a plurality of systems of lens units 11401 are provided corresponding to the individual image pickup elements.

Further, the image pickup unit 11402 may not necessarily be provided on the camera head 11102. For example, the image pickup unit 11402 may be provided immediately behind the objective lens in the inside of the lens barrel 11101.

The driving unit 11403 includes an actuator and moves the zoom lens and the focusing lens of the lens unit 11401 by a predetermined distance along an optical axis under the control of the camera head controlling unit 11405. Consequently, the magnification and the focal point of a picked up image by the image pickup unit 11402 can be adjusted suitably.

The communication unit 11404 includes a communication apparatus for transmitting and receiving various kinds of information to and from the CCU 11201. The communication unit 11404 transmits an image signal acquired from the image pickup unit 11402 as RAW data to the CCU 11201 through the transmission cable 11400.

In addition, the communication unit 11404 receives a control signal for controlling driving of the camera head 11102 from the CCU 11201 and supplies the control signal to the camera head controlling unit 11405. The control signal includes information relating to image pickup conditions such as, for example, information that a frame rate of a picked up image is designated, information that an exposure value upon image picking up is designated and/or information that a magnification and a focal point of a picked up image are designated.

It is to be noted that the image pickup conditions such as the frame rate, exposure value, magnification or focal point may be designated by the user or may be set automatically by the control unit 11413 of the CCU 11201 on the basis of an acquired image signal. In the latter case, an auto exposure (AE) function, an auto focus (AF) function and an auto white balance (AWB) function are incorporated in the endoscope 11100.

The camera head controlling unit 11405 controls driving of the camera head 11102 on the basis of a control signal from the CCU 11201 received through the communication unit 11404.

The communication unit 11411 includes a communication apparatus for transmitting and receiving various kinds of information to and from the camera head 11102. The communication unit 11411 receives an image signal transmitted thereto from the camera head 11102 through the transmission cable 11400.

Further, the communication unit 11411 transmits a control signal for controlling driving of the camera head 11102 to the camera head 11102. The image signal and the control signal can be transmitted by electrical communication, optical communication or the like.

The image processing unit 11412 performs various image processes for an image signal in the form of RAW data transmitted thereto from the camera head 11102.

The control unit 11413 performs various kinds of control relating to image picking up of a surgical region or the like by the endoscope 11100 and display of a picked up image obtained by image picking up of the surgical region or the like. For example, the control unit 11413 creates a control signal for controlling driving of the camera head 11102.

Further, the control unit 11413 controls, on the basis of an image signal for which image processes have been performed by the image processing unit 11412, the display apparatus 11202 to display a picked up image in which the surgical region or the like is imaged. Thereupon, the control unit 11413 may recognize various objects in the picked up image using various image recognition technologies. For example, the control unit 11413 can recognize a surgical tool such as forceps, a particular living body region, bleeding, mist when the energy device 11112 is used and so forth by detecting the shape, color and so forth of edges of objects included in a picked up image. The control unit 11413 may cause, when it controls the display apparatus 11202 to display a picked up image, various kinds of surgery supporting information to be displayed in an overlapping manner with an image of the surgical region using a result of the recognition. Where surgery supporting information is displayed in an overlapping manner and presented to the surgeon 11131, the burden on the surgeon 11131 can be reduced and the surgeon 11131 can proceed with the surgery with certainty.

The transmission cable 11400 which connects the camera head 11102 and the CCU 11201 to each other is an electric signal cable ready for communication of an electric signal, an optical fiber ready for optical communication or a composite cable ready for both of electrical and optical communications.

Here, while, in the example depicted, communication is performed by wired communication using the transmission cable 11400, the communication between the camera head 11102 and the CCU 11201 may be performed by wireless communication.

An example of an endoscopic surgery system to which the technology according to the present disclosure can be applied has been described. The technology according to the present disclosure can be applied to the endoscope 11100 or the (image pickup unit 11402 of the) camera head 11102 from within the configuration described hereinabove. For example, the solid-state imaging element 1 of FIG. 16 can be applied to the endoscope 11100 or (the image pickup unit 11402 of) the camera head 11102. By applying the technology according to the present disclosure to the endoscope 11100 or (the image pickup unit 11402 of) the camera head 11102, it is possible to sufficiently secure a time width of a pulse signal and reduce a pixel size, and therefore, for example, the apparatus can be downsized. Further, it is possible to achieve reduction of power consumption.

It is to be noted that, while an endoscopic surgery system is described here as an example, the technology according to the present disclosure can be applied, for example, to a microsurgery system.

6. Application Example to Moving Body

The technology according to the present disclosure (present technology) can be applied to various products. For example, the technology according to the present disclosure may be implemented as an apparatus that is incorporated in any type of moving body such as an automobile, an electric car, a hybrid electric car, a motorcycle, a bicycle, a personal mobility, an airplane, a drone, a ship, or a robot.

Figure 22:
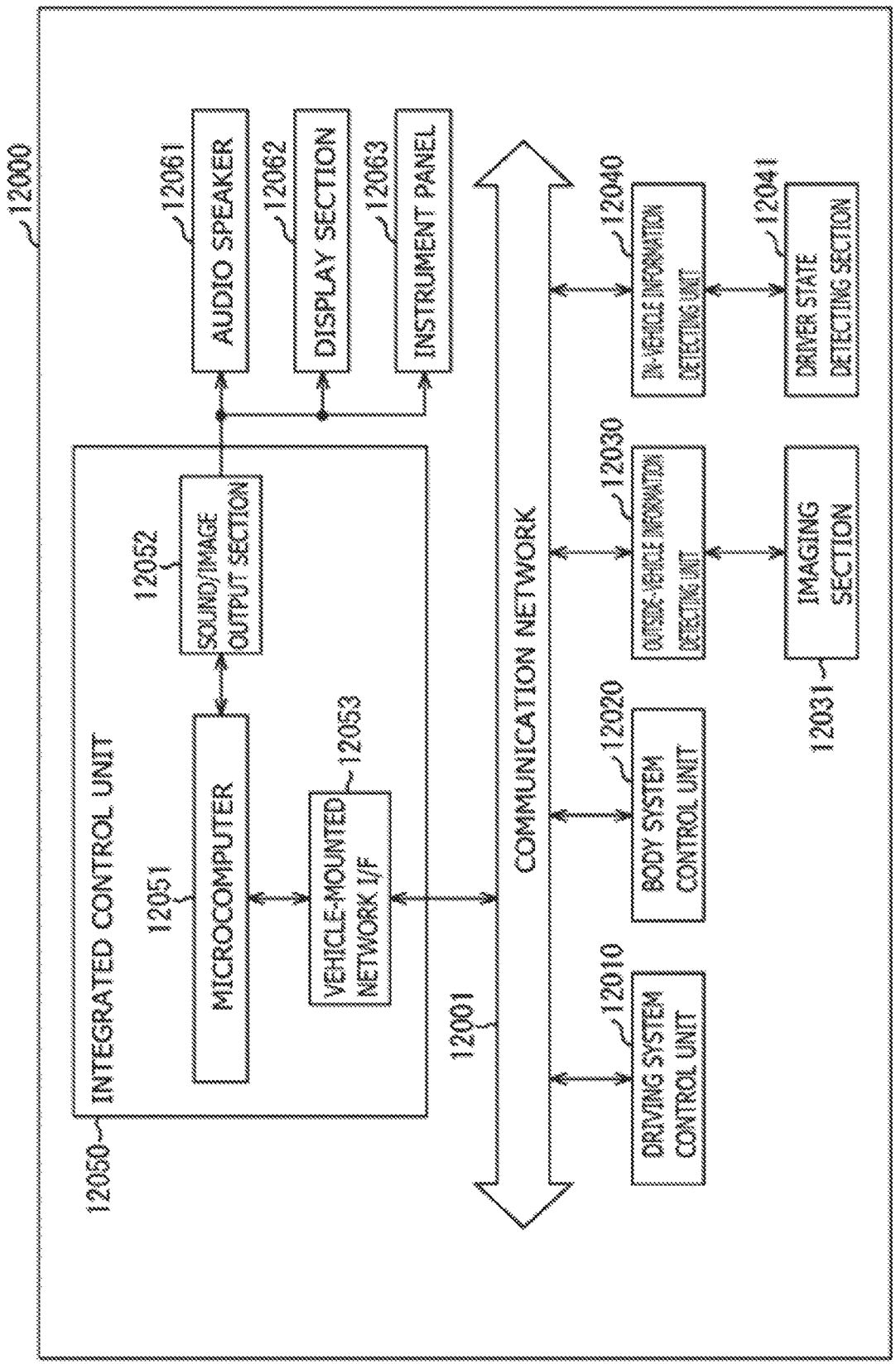
FIG. 22 is a block diagram depicting an example of schematic configuration of a vehicle control system.

FIG. 22 is a block diagram depicting an example of schematic configuration of a vehicle control system as an example of a mobile body control system to which the technology according to an embodiment of the present disclosure can be applied.

The vehicle control system 12000 includes a plurality of electronic control units connected to each other via a communication network 12001. In the example depicted in FIG. 22, the vehicle control system 12000 includes a driving system control unit 12010, a body system control unit 12020, an outside-vehicle information detecting unit 12030, an in-vehicle information detecting unit 12040, and an integrated control unit 12050. In addition, a microcomputer 12051, a sound/image output section 12052, and a vehicle-mounted network interface (I/F) 12053 are illustrated as a functional configuration of the integrated control unit 12050.

The driving system control unit 12010 controls the operation of devices related to the driving system of the vehicle in accordance with various kinds of programs. For example, the driving system control unit 12010 functions as a control device for a driving force generating device for generating the driving force of the vehicle, such as an internal combustion engine, a driving motor, or the like, a driving force transmitting mechanism for transmitting the driving force to wheels, a steering mechanism for adjusting the steering angle of the vehicle, a braking device for generating the braking force of the vehicle, and the like.

The body system control unit 12020 controls the operation of various kinds of devices provided to a vehicle body in accordance with various kinds of programs. For example, the body system control unit 12020 functions as a control device for a keyless entry system, a smart key system, a power window device, or various kinds of lamps such as a headlamp, a backup lamp, a brake lamp, a turn signal, a fog lamp, or the like. In this case, radio waves transmitted from a mobile device as an alternative to a key or signals of various kinds of switches can be input to the body system control unit 12020. The body system control unit 12020 receives these input radio waves or signals, and controls a door lock device, the power window device, the lamps, or the like of the vehicle.

The outside-vehicle information detecting unit 12030 detects information about the outside of the vehicle including the vehicle control system 12000. For example, the outside-vehicle information detecting unit 12030 is connected with an imaging section 12031. The outside-vehicle information detecting unit 12030 makes the imaging section 12031 image an image of the outside of the vehicle, and receives the imaged image. On the basis of the received image, the outside-vehicle information detecting unit 12030 may perform processing of detecting an object such as a human, a vehicle, an obstacle, a sign, a character on a road surface, or the like, or processing of detecting a distance thereto.

The imaging section 12031 is an optical sensor that receives light, and which outputs an electric signal corresponding to a received light amount of the light. The imaging section 12031 can output the electric signal as an image, or can output the electric signal as information about a measured distance. In addition, the light received by the imaging section 12031 may be visible light, or may be invisible light such as infrared rays or the like.

The in-vehicle information detecting unit 12040 detects information about the inside of the vehicle. The in-vehicle information detecting unit 12040 is, for example, connected with a driver state detecting section 12041 that detects the state of a driver. The driver state detecting section 12041, for example, includes a camera that images the driver. On the basis of detection information input from the driver state detecting section 12041, the in-vehicle information detecting unit 12040 may calculate a degree of fatigue of the driver or a degree of concentration of the driver, or may determine whether the driver is dozing.

The microcomputer 12051 can calculate a control target value for the driving force generating device, the steering mechanism, or the braking device on the basis of the information about the inside or outside of the vehicle which information is obtained by the outside-vehicle information detecting unit 12030 or the in-vehicle information detecting unit 12040, and output a control command to the driving system control unit 12010. For example, the microcomputer 12051 can perform cooperative control intended to implement functions of an advanced driver assistance system (ADAS) which functions include collision avoidance or shock mitigation for the vehicle, following driving based on a following distance, vehicle speed maintaining driving, a warning of collision of the vehicle, a warning of deviation of the vehicle from a lane, or the like.

In addition, the microcomputer 12051 can perform cooperative control intended for automatic driving, which makes the vehicle to travel autonomously without depending on the operation of the driver, or the like, by controlling the driving force generating device, the steering mechanism, the braking device, or the like on the basis of the information about the outside or inside of the vehicle which information is obtained by the outside-vehicle information detecting unit 12030 or the in-vehicle information detecting unit 12040.

In addition, the microcomputer 12051 can output a control command to the body system control unit 12020 on the basis of the information about the outside of the vehicle which information is obtained by the outside-vehicle information detecting unit 12030. For example, the microcomputer 12051 can perform cooperative control intended to prevent a glare by controlling the headlamp so as to change from a high beam to a low beam, for example, in accordance with the position of a preceding vehicle or an oncoming vehicle detected by the outside-vehicle information detecting unit 12030.

The sound/image output section 12052 transmits an output signal of at least one of a sound and an image to an output device capable of visually or auditorily notifying information to an occupant of the vehicle or the outside of the vehicle. In the example of FIG. 22, an audio speaker 12061, a display section 12062, and an instrument panel 12063 are illustrated as the output device. The display section 12062 may, for example, include at least one of an on-board display and a head-up display.

Figure 23:
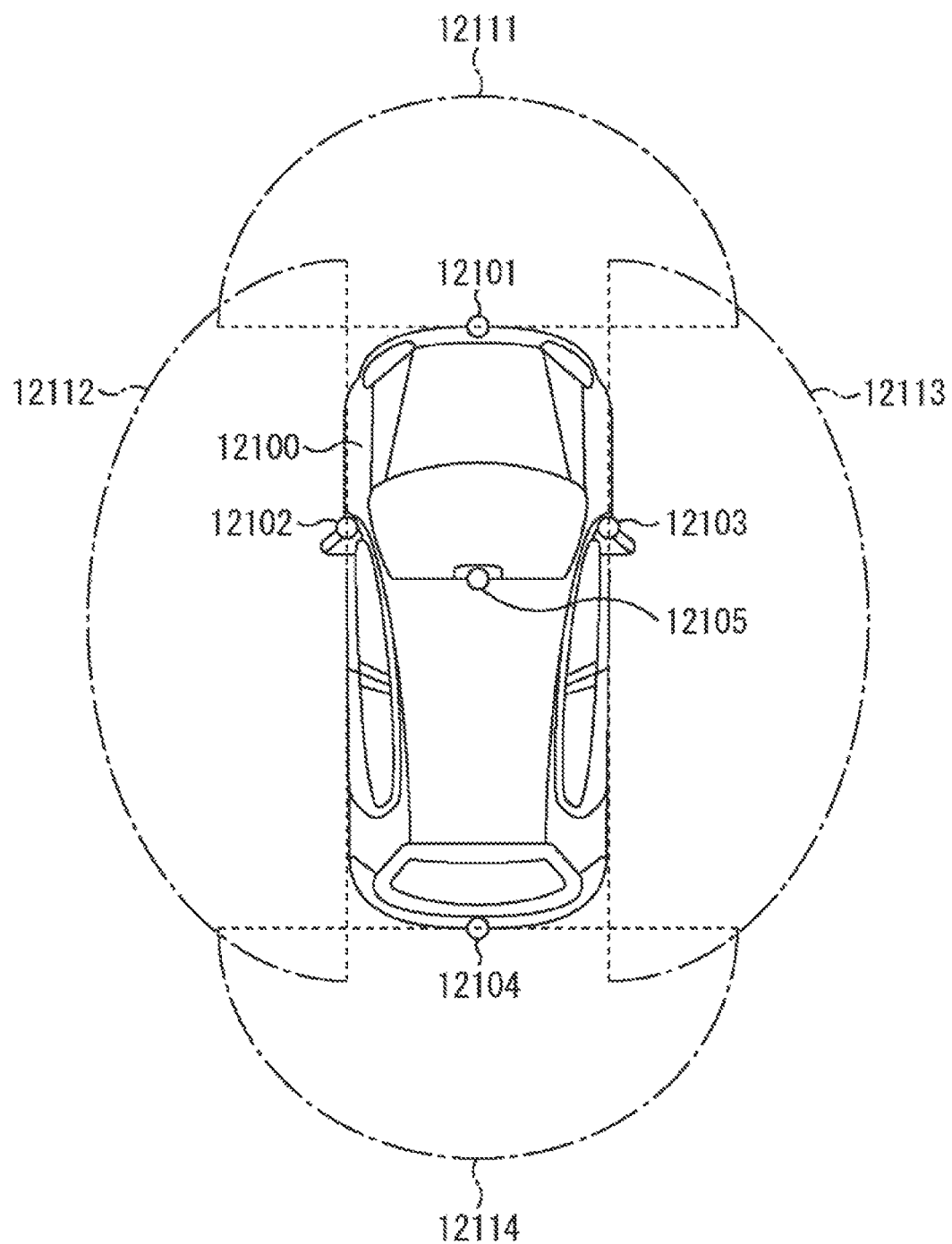
FIG. 23 is a diagram of assistance in explaining an example of installation positions of an outside-vehicle information detecting section and an imaging section.

FIG. 23 is a diagram depicting an example of the installation position of the imaging section 12031.

In FIG. 23, the imaging section 12031 includes imaging sections 12101, 12102, 12103, 12104, and 12105.

The imaging sections 12101, 12102, 12103, 12104, and 12105 are, for example, disposed at positions on a front nose, sideview mirrors, a rear bumper, and a back door of the vehicle 12100 as well as a position on an upper portion of a windshield within the interior of the vehicle. The imaging section 12101 provided to the front nose and the imaging section 12105 provided to the upper portion of the windshield within the interior of the vehicle obtain mainly an image of the front of the vehicle 12100. The imaging sections 12102 and 12103 provided to the sideview mirrors obtain mainly an image of the sides of the vehicle 12100. The imaging section 12104 provided to the rear bumper or the back door obtains mainly an image of the rear of the vehicle 12100. The imaging section 12105 provided to the upper portion of the windshield within the interior of the vehicle is used mainly to detect a preceding vehicle, a pedestrian, an obstacle, a signal, a traffic sign, a lane, or the like.

Incidentally, FIG. 23 depicts an example of photographing ranges of the imaging sections 12101 to 12104. An imaging range 12111 represents the imaging range of the imaging section 12101 provided to the front nose. Imaging ranges 12112 and 12113 respectively represent the imaging ranges of the imaging sections 12102 and 12103 provided to the sideview mirrors. An imaging range 12114 represents the imaging range of the imaging section 12104 provided to the rear bumper or the back door. A bird's-eye image of the vehicle 12100 as viewed from above is obtained by superimposing image data imaged by the imaging sections 12101 to 12104, for example.

At least one of the imaging sections 12101 to 12104 may have a function of obtaining distance information. For example, at least one of the imaging sections 12101 to 12104 may be a stereo camera constituted of a plurality of imaging elements, or may be an imaging element having pixels for phase difference detection.

For example, the microcomputer 12051 can determine a distance to each three-dimensional object within the imaging ranges 12111 to 12114 and a temporal change in the distance (relative speed with respect to the vehicle 12100) on the basis of the distance information obtained from the imaging sections 12101 to 12104, and thereby extract, as a preceding vehicle, a nearest three-dimensional object in particular that is present on a traveling path of the vehicle 12100 and which travels in substantially the same direction as the vehicle 12100 at a predetermined speed (for example, equal to or more than 0 km/hour). Further, the microcomputer 12051 can set a following distance to be maintained in front of a preceding vehicle in advance, and perform automatic brake control (including following stop control), automatic acceleration control (including following start control), or the like. It is thus possible to perform cooperative control intended for automatic driving that makes the vehicle travel autonomously without depending on the operation of the driver or the like.

For example, the microcomputer 12051 can classify three-dimensional object data on three-dimensional objects into three-dimensional object data of a two-wheeled vehicle, a standard-sized vehicle, a large-sized vehicle, a pedestrian, a utility pole, and other three-dimensional objects on the basis of the distance information obtained from the imaging sections 12101 to 12104, extract the classified three-dimensional object data, and use the extracted three-dimensional object data for automatic avoidance of an obstacle. For example, the microcomputer 12051 identifies obstacles around the vehicle 12100 as obstacles that the driver of the vehicle 12100 can recognize visually and obstacles that are difficult for the driver of the vehicle 12100 to recognize visually. Then, the microcomputer 12051 determines a collision risk indicating a risk of collision with each obstacle. In a situation in which the collision risk is equal to or higher than a set value and there is thus a possibility of collision, the microcomputer 12051 outputs a warning to the driver via the audio speaker 12061 or the display section 12062, and performs forced deceleration or avoidance steering via the driving system control unit 12010. The microcomputer 12051 can thereby assist in driving to avoid collision.

At least one of the imaging sections 12101 to 12104 may be an infrared camera that detects infrared rays. The microcomputer 12051 can, for example, recognize a pedestrian by determining whether or not there is a pedestrian in imaged images of the imaging sections 12101 to 12104. Such recognition of a pedestrian is, for example, performed by a procedure of extracting characteristic points in the imaged images of the imaging sections 12101 to 12104 as infrared cameras and a procedure of determining whether or not it is the pedestrian by performing pattern matching processing on a series of characteristic points representing the contour of the object. When the microcomputer 12051 determines that there is a pedestrian in the imaged images of the imaging sections 12101 to 12104, and thus recognizes the pedestrian, the sound/image output section 12052 controls the display section 12062 so that a square contour line for emphasis is displayed so as to be superimposed on the recognized pedestrian. The sound/image output section 12052 may also control the display section 12062 so that an icon or the like representing the pedestrian is displayed at a desired position.

An example of a vehicle control system to which the technology according to the present disclosure can be applied has been described. The technology according to the present disclosure can be applied, for example, to the imaging section 12031 (including the imaging sections 12101 to 12104) or the like from within the configuration described above. In particular, for example, the solid-state imaging element 1 of FIG. 16 can be applied to the imaging section 12031 (including the imaging sections 12101 to 12104). By applying the technology according to the present disclosure to the imaging section 12031 (including the imaging sections 12101 to 12104), it is possible to sufficiently secure a time width of a pulse signal and reduce a pixel size, and therefore, for example, the apparatus can be downsized. Further, it is possible to achieve reduction of power consumption.

It is to be noted that, in the present specification, the steps that describe the series of processes described hereinabove not only include processes that are performed in a time series in accordance with the order described but also include processes that are executed in parallel or individually even if they are not necessarily be processed in a time series.

Further, the embodiment in the present disclosure is not limited to the embodiments described hereinabove and can be altered in various manners without departing from the subject matter of the present disclosure.

Further, a component described as one apparatus (or processing section) in the foregoing description may be divided so as to be configured as a plurality of apparatuses (or processing sections). Conversely, components described as a plurality of apparatuses (or processing sections) in the foregoing description may be collected so as to be configured as a single apparatus (or processing section). Naturally, a component other than those described hereinabove may be added to the configuration of each apparatus (or each processing section). Furthermore, if a configuration or operation as an entire system is substantially same, part of components of a certain apparatus (or processing section) may be included in a configuration of some other apparatus (or some other processing section). In short, the present technology is not limited to the embodiments described above and can be altered in various manners without departing from the subject matter of the present technology.

Although the preferred embodiments of the present disclosure have been described in detail with reference to the accompanying drawings, the disclosure is not limited to such examples as described above. It is apparent that persons who have common knowledge in the technical field to which the present disclosure pertains could have conceived various alterations or modifications within the scope of the technical idea described in the claims, and it is understood that those naturally fall within the technical scope of the present disclosure.

It is to be noted that the present disclosure can assume such a configuration as described below.

(1) A solid-state imaging element, including:
 a pixel array section in which unit pixels each having a photoelectric conversion section are disposed; and
 an AD converter for each of the unit pixels, in which the AD converter includes
  a pulse generation circuit that feeds back a delay signal obtained by delaying an output signal of a comparator to the comparator and performs arithmetic operation of the output signal and the delay signal to generate a pulse signal, and
  a latch circuit that latches a data code using the pulse signal generated by the pulse generation circuit.

(2) The solid-state imaging element according to (1) above, in which
 the pulse generation circuit includes:
  a delay element that delays the output signal of the comparator to generate the delay signal; and
  an arithmetic element that arithmetically operates the output signal and the delay signal to generate the pulse signal.

(3) The solid-state imaging element according to (2) above, in which
 the arithmetic element includes a NOR circuit.

(4) The solid-state imaging element according to (2) above, in which
 the arithmetic element includes a NAND circuit.

(5) The solid-state imaging element according to any one of (1) to (4) above, in which
 in the pulse generation circuit, a logical threshold value of a gate element is adjusted.

(6) The solid-state imaging element according to (5) above, in which
 in the pulse generation circuit, the logical threshold value of the gate element is adjusted by changing an element number of transistors.

(7) The solid-state imaging element according to (5) above, in which
 in the pulse generation circuit, the logical threshold value of the gate element is adjusted by setting the threshold value of the elements of transistors to a high threshold value and a low threshold value.

(8) The solid-state imaging element according to any one of (1) to (7) above, in which
 the pulse generation circuit further includes a selection circuit that selects a path used when a delay signal obtained by delaying the output signal of the comparator is to be fed back to the comparator and the output signal and the delay signal are arithmetically operated to generate a pulse signal and another path used when the output signal of the comparator is to be used as it is.

(9) The solid-state imaging element according to any one of (1) to (8) above, in which
 the solid-state imaging element includes a stacked type solid-state imaging element.

(10) Electronic equipment including:
 a solid-state imaging element including
  a pixel array section in which unit pixels each having a photoelectric conversion section are disposed, and
  an AD converter for each of the unit pixels, in which the AD converter includes a pulse generation circuit that feeds back a delay signal obtained by delaying an output signal of a comparator to the comparator and performs arithmetic operation of the output signal and the delay signal to generate a pulse signal, and a latch circuit that latches a data code using the pulse signal generated by the pulse generation circuit;

a signal processing circuit that processes an output signal outputted from the solid-state imaging element; and an optical system that enters incident light into the solid-state imaging element.

REFERENCE SIGNS LIST

1 Solid-state imaging element, 3 Pixel region, 8 Control circuit, 22 Comparator, 23 Auto zero, 24 PFB, 25 Pulse generation circuit, 26 Latch circuit, 31 Repeater, 32 RAM CDS, 33 Gray Code, 40 Comparison circuit, 41, 41-1, 41-2 Delay element, 42 Arithmetic element, 43 Inversion element, 51 AD converter, 61 AD conversion device, 71, 72 Inverter, 81 Upper chip, 85 Selector circuit, 101 Upper chip, 102 Lower chip, 111 Logic circuit, 300 Electronic equipment, 301 Solid-state imaging device, 302 Optical lens, 303 Shutter device, 304 Driving circuit, 305 Signal processing circuit

The invention claimed is:

1. A light detecting device, comprising:
a first substrate that includes four pixels and a first part of a comparison circuit, wherein the first part of the comparison circuit is coupled to the four pixels;
a second substrate laminated to the first substrate, wherein the second substrate includes a second part of the comparison circuit, and
the second part of the comparison circuit is coupled to the first part of the comparison circuit; and
an AD converter that includes the first part of the comparison circuit and the second part of the comparison circuit, wherein
the AD converter is shared by the four pixels, and
the AD converter further includes:
a pulse generation circuit configured to:
feed back a delay signal to a comparator circuit, wherein the delay signal represents an output signal of the comparison circuit with a specific delay; and
generate a pulse signal; and
a latch circuit configured to latch a data code based on the generated pulse signal.

2. The light detection device according to claim 1, wherein the pulse generation circuit includes:
a delay element configured to delay the output signal of the comparator circuit to generate the delay signal; and
an arithmetic element configured to arithmetically operate the output signal and the delay signal to generate the pulse signal.

3. The light detection device according to claim 2, wherein the arithmetic element includes a NOR circuit.

4. The light detection device according to claim 2, wherein the arithmetic element includes a NAND circuit.

5. The light detection device according to claim 1, wherein in the pulse generation circuit, a logical threshold value of a gate element is adjustable.

6. The light detection device according to claim 5, wherein in the pulse generation circuit, the logical threshold value of the gate element is adjustable based on an element number of transistors.

7. The light detection device according to claim 5, wherein
in the pulse generation circuit, the logical threshold value of the gate element is adjustable based a threshold value of each of elements of transistors, and
each of the elements of the transistors is changeable to a high threshold value and a low threshold value.

8. The light detection device according to claim 2, wherein the pulse generation circuit further includes a selection circuit configured to:
select a first path when the delay signal is to be feed back to the comparator circuit and when the output signal and the delay signal are arithmetically operated to generate the pulse signal; and
select a second path when the output signal of the comparator circuit is to be used as it is.

9. Electronic equipment, comprising:
a light detecting device including:
a first substrate that includes four pixels and a first part of a comparison circuit, wherein the first part of the comparison circuit is coupled to the four pixels;
a second substrate laminated to the first substrate, wherein
the second substrate includes a second part of the comparison circuit, and
the second part of the comparison circuit is coupled to the first part of the comparison circuit; and
an AD converter that includes the first part of the comparison circuit and the second part of the comparison circuit, wherein
the AD converter is shared by the four pixels, and
the AD converter further includes:
a pulse generation circuit configured to:
feed back a delay signal to a comparator circuit, wherein the delay signal represents an output signal of the comparison circuit with a specific delay; and
generate a pulse signal; and
a latch circuit configured to latch a data code based on the generated pulse signal;
a signal processing circuit configured to process the data code; and
an optical system configured to enter incident light into the light detecting device.

* * * * *